US012186132B2

(12) United States Patent
Naidu et al.

(10) Patent No.: US 12,186,132 B2
(45) Date of Patent: Jan. 7, 2025

(54) POINT-OF-CARE ULTRASOUND (POCUS) SCAN ASSISTANCE AND ASSOCIATED DEVICES, SYSTEMS, AND METHODS

(71) Applicant: KONINKLIJKE PHILIPS N.V., Eindhoven (NL)

(72) Inventors: Raghavendra Srinivasa Naidu, Auburndale, MA (US); Jochen Kruecker, Andover, MA (US); Man Nguyen, Melrose, MA (US); Claudia Errico, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 235 days.

(21) Appl. No.: 17/775,695

(22) PCT Filed: Nov. 17, 2020

(86) PCT No.: PCT/EP2020/082310
§ 371 (c)(1),
(2) Date: May 10, 2022

(87) PCT Pub. No.: WO2021/099278
PCT Pub. Date: May 27, 2021

(65) Prior Publication Data
US 2022/0401062 A1    Dec. 22, 2022

Related U.S. Application Data

(60) Provisional application No. 62/938,533, filed on Nov. 21, 2019.

(51) Int. Cl.
*A61B 8/08*   (2006.01)
*A61B 8/00*   (2006.01)
(Continued)

(52) U.S. Cl.
CPC ............ *A61B 8/5223* (2013.01); *A61B 8/085* (2013.01); *A61B 8/4245* (2013.01); *G06V 10/22* (2022.01); *G06V 10/82* (2022.01)

(58) Field of Classification Search
CPC ..... A61B 8/5223; A61B 8/085; A61B 8/4245; G06V 10/82; G06V 10/22
See application file for complete search history.

(56) References Cited

U.S. PATENT DOCUMENTS

2009/0024030 A1    1/2009  Lachaine et al.
2017/0143312 A1*   5/2017  Hedlund ............... A61B 6/487
(Continued)

OTHER PUBLICATIONS

International Search Report and Written Opinion for PCT/EP2020/082310, Mailing date: Feb. 16, 2021, 9 pages.

*Primary Examiner* — Chao Sheng

(57) ABSTRACT

Ultrasound image devices, systems, and methods are provided. An ultrasound imaging system comprising a processor circuit in communication with an ultrasound probe comprising a transducer array, wherein the processor circuit is configured to receive, from the ultrasound probe, a first image of a patients anatomy; detect, from the first image, a first anatomical landmark at a first location along a scanning trajectory of the patients anatomy; determine, based on the first anatomical landmark, a steering configuration for steering the ultrasound probe towards a second anatomical landmark at a second location along the scanning trajectory; and output, to a display in communication with the processor circuit, an instruction based on the steering configuration to steer the ultrasound probe towards the second anatomical landmark at the second location.

20 Claims, 12 Drawing Sheets

(51) Int. Cl.
    *G06V 10/22*     (2022.01)
    *G06V 10/82*     (2022.01)

(56) References Cited

U.S. PATENT DOCUMENTS

2017/0360401 A1   12/2017   Rothberg et al.
2019/0125301 A1    5/2019   Jago et al.

\* cited by examiner

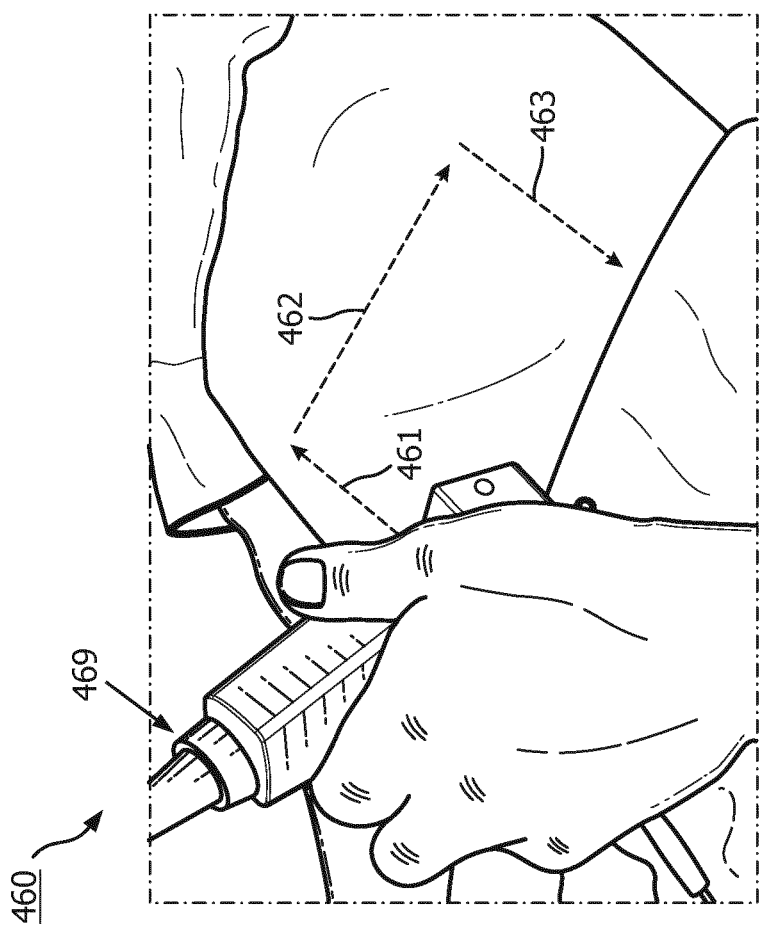

POINT-OF-CARE ULTRASOUND (POCUS) SCAN ASSISTANCE AND ASSOCIATED DEVICES, SYSTEMS, AND METHODS

CROSS-REFERENCE TO PRIOR APPLICATIONS

This application is the U.S. National Phase application under 35 U.S.C. § 371 of International Application No. PCT/EP2020/082310, filed on Nov. 17, 2020, which claims the benefit of U.S. Provisional Patent Application No. 62/938,533, filed on Nov. 21, 2019. These applications are hereby incorporated by reference herein.

TECHNICAL FIELD

The present disclosure relates generally to ultrasound imaging and, in particular, to providing automatic, systematic scan guidance for using ultrasound imaging in clinical assessments.

BACKGROUND

Ultrasound imaging systems are widely used for medical imaging. For example, a medical ultrasound system may include an ultrasound transducer probe coupled to a processing system and one or more display devices. The ultrasound transducer probe may include an array of ultrasound transducer elements that transmit acoustic waves into a patient's body and record acoustic waves reflected from the internal anatomical structures within the patient's body, which may include tissues, blood vessels, and internal organs. The transmission of the acoustic waves and/or the reception of reflected acoustic waves or echo responses can be performed by the same set of ultrasound transducer elements or different sets of ultrasound transducer elements. The processing system can apply beamforming, signal processing, and/or imaging processing to the received echo responses to create an image of the patient's internal anatomical structures. The image may be presented to a clinician in the form of a brightness-mode (B-mode) image, where each pixel of the image is represented by a brightness level or intensity level corresponding to the echo strength.

Ultrasound imaging is a safe and useful tool for diagnostic examination, interventions, and/or treatment. For instance, appendicitis and intussusception have high variability in clinical presentations, and thus can be challenging to diagnose such conditions. Blindly taking a patient to surgery without any imaging can lead to a negative laparotomy, which may cause complications. Thus, the current clinical guidelines stipulate that ultrasound be the first line imaging modality if such appendicitis and/or intussusception conditions are suspected. The rapid growth in point-of-care (POCUS) has enabled the availability of ultrasound twenty-four hours in many point-of-care settings, such as during an emergency situation and/or at a critical care unit. However, use of POCUS can be challenging for emergency physicians, specifically for novice users, in terms of sufficient scan coverage, structure identification, and rapid assessment of the condition.

SUMMARY

There remains a clinical need for improved systems and techniques for providing systematic imaging guidance in clinical examinations. Embodiments of the present disclosure provide techniques for systematic scan guidance for diagnosing a clinical condition. The assessment of a clinical condition may be required to follow a certain scanning topography or scanning trajectory. For instance, the scanning for an appendicitis assessment may require the scanning of a right-lower-quadrant (RLQ) of a patient's abdomen. Alternatively, the scanning for an intussusception may require the scanning of all quadrants of a patient's abdomen. The scanning topography or scanning trajectory may include a series of anatomical landmarks that may be relevant to the evaluation or may lead to a target anatomical site for the evaluation. The disclosed embodiments automatically detect or search for anatomical landmarks from acquired image frame(s) and guide a user in performing a systematic scan of the clinical condition based on the detected anatomical landmarks. In some aspects, the disclosed embodiments use a deep learning prediction network to perform the automatic anatomical landmark detection and infer a probe steering configuration based on detected anatomical landmark(s). The disclosed embodiments may provide the user with visual guidance for the scan based on the inferred probe steering configuration. The visual guidance can be in the form of displaying directional arrows for translations and/or rotations, textual displays, and/or audio alerts. Additionally, the disclosed embodiments can automatically select image frame(s) that are representative of a normal clinical condition and/or an abnormal clinical condition from the acquired images and present the selected image frame(s) to the user such that the user may perform a quicker diagnosis. Further, the disclosed embodiments can automatically adjust ultrasound signal settings (e.g., signal gain and/or imaging depth of field) to provide optimal imaging quality for the scan. While the disclosed embodiments are described in the context of appendicitis and/or intussusception assessments, the disclosed embodiments are suitable for providing scanning assistance to assessments of other clinical conditions in other anatomies of a patient using. Additionally, the disclosed embodiments can be applied to POCUS systems and/or any other types of ultrasound imaging systems.

In one embodiment, an ultrasound imaging system includes a processor circuit in communication with an ultrasound probe including a transducer array, where the processor circuit is configured to receive, from the ultrasound probe, a first image of a patient's anatomy; detect, from the first image, a first anatomical landmark at a first location along a scanning trajectory of the patient's anatomy; determine, based on the first anatomical landmark, a steering configuration for steering the ultrasound probe towards a second anatomical landmark at a second location along the scanning trajectory; and output, to a display in communication with the processor circuit, an instruction based on the steering configuration to steer the ultrasound probe towards the second anatomical landmark at the second location.

In some aspects, the system may also include where the steering configuration includes at least one of a rotation or a translation. In some aspects, the system may also include a probe controller in communication with the ultrasound probe and the processor circuit, where the transducer array is a two-dimensional (2D) transducer array, and where the processor circuit is configured to receive, from the ultrasound probe, a second image of the patient's anatomy at the second location, the second image including the second anatomical landmark; determine, based on the second image, a beam steering angle to steer ultrasound beams of the transducer array towards a third anatomical landmark at a third location along the scanning trajectory; and output, to the probe controller, an instruction to configure the transducer array based on the beam steering angle. In some aspects, the system may also include a probe controller in communication with the ultrasound probe and the processor circuit, where the processor circuit is configured to determine an ultrasound signal adjustment for the transducer array based on the first image; and output, to the probe controller, an instruction to configure the transducer array based on the ultrasound signal adjustment. In some aspects, the system may also include where the ultrasound signal adjustment is associated with at least one of a signal gain or an imaging depth of field. In some aspects, the system may also include a memory in communication with the processor circuit, where the processor circuit is configured to receive, from the ultrasound probe, a second image of the patient's anatomy based on the steering configuration; determine that the second image includes an anatomical feature representative of a clinical condition; and store, at the memory, the second image based on determining that the second image includes the anatomical feature representative of the clinical condition. In some aspects, the system may also include where the processor circuit is configured to output, to the display, the second image based on determining that the second image includes the anatomical feature representative of the clinical condition. In some aspects, the system may also include where the processor circuit configured to detect the first anatomical landmark and determine the steering configuration is configured to apply a predictive network to the first image, the predictive network trained for at least one of an anatomical landmark detection or a steering configuration prediction associated with the scanning trajectory. In some aspects, the system may also include a probe controller in communication with the ultrasound probe and the processor circuit, where the processor circuit is configured to receive, from the ultrasound probe, a second image of the patient's anatomy at the second location, the second image including the second anatomical landmark; apply a predictive network to the second image, the predictive network trained for beam steering prediction; and output, to the probe controller, an instruction to configure the transducer array based on an output of the predictive network. In some aspects, the system may also include a probe controller in communication with the ultrasound probe and the processor circuit, where the processor circuit is configured to receive, from the ultrasound probe, a second image of the patient's anatomy based on the steering configuration; apply a predictive network to the second image, the predictive network trained for at least one of an ultrasound signal gain adjustment or an imaging depth of field adjustment; and output, to the probe controller, an instruction to configure the transducer array based on an output of the predictive network. In some aspects, the system may also include a memory in communication with the processor circuit, where the processor circuit is configured to receive, from the ultrasound probe, a second image of the patient's anatomy based on the steering configuration; apply a predictive network to the second image, the predictive network trained to identify a clinical condition; and store, at the memory, the second image based on an output of the predictive network. In some aspects, the system may also include where the processor circuit configured to output the instruction is configured to output, to the display, a map of the scanning trajectory and at least one of a visual motion indicator with respect to the scanning trajectory based on the instruction, a location of the transducer array with respect to the scanning trajectory, or an orientation of the transducer array with respect to the scanning trajectory. In some aspects, the system may also include where the patient's anatomy includes an abdominal region of the patient, and where the scanning trajectory traverses at least one of a right upper quadrant (RUQ), a right lower quadrant (RLQ), a left upper quadrant (LUQ), or a left lower quadrant (LLQ) of the patient's abdominal region. In some aspects, the system may also include where the scanning trajectory is associated with an appendicitis examination, and where the first anatomical landmark includes at least one of a liver; an ascending colon; a cecum pouch; a terminal ileum; an appendix; or an anatomical characteristic of an appendicitis. In some aspects, the system may also include where the scanning trajectory is associated with an intussusception examination, and where the first anatomical landmark includes at least one of a psoas muscle; an ascending colon; a liver; a gallbladder; an epigastrium; a descending colon; or an anatomical characteristic of an intussusception.

In one embodiment, a method of ultrasound imaging, includes receiving, at a processor circuit in communication with an ultrasound probe including a transducer array, a first image of a patient's anatomy; detecting, at the processor circuit from the first image, a first anatomical landmark at a first location along a scanning trajectory of the patient's anatomy; determining, at the processor circuit based on the first anatomical landmark, a steering configuration for steering the ultrasound probe towards a second anatomical landmark at a second location along the scanning trajectory; and outputting, to a display in communication with the processor circuit, an instruction based on the steering configuration to steer the ultrasound probe towards the second anatomical landmark at the second location.

In some aspects, the method may also include where the steering configuration includes at least one of a rotation or a translation. In some aspects, the method may also include receiving, at the processor circuit from the ultrasound probe, a second image of the patient's anatomy at the second location, the second image including the second anatomical landmark; determining, at the processor circuit based on the second image, a beam steering angle to steer ultrasound beams of the transducer array towards a third anatomical landmark at a third location along the scanning trajectory; and outputting, to a probe controller in communication with the processor circuit and the ultrasound probe, an instruction to configure the transducer array based on the beam steering angle. In some aspects, the method may also include determining, at the processor circuit, an ultrasound signal adjustment for the transducer array based on the first image, the ultrasound signal adjustment associated with at least one a signal gain or an imaging depth of field; and outputting, to a probe controller in communication with the processor circuit and the ultrasound probe, an instruction to configure the transducer array based on the ultrasound signal adjustment. In some aspects, the method may also include receiving, at the processor circuit from the ultrasound probe, a second image of the patient's anatomy based on the steering configuration; determining, at the processor circuit, that the second image includes an anatomical feature representative of a clinical condition; and storing, at a memory in communication with the processor circuit, the second image based on determining that the second image includes the anatomical feature representative of the clinical condition.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 4C is a schematic diagram illustrating a scanning trajectory for an intussusception assessment, according to aspects of the present disclosure.

DETAILED DESCRIPTION

Figure 1:
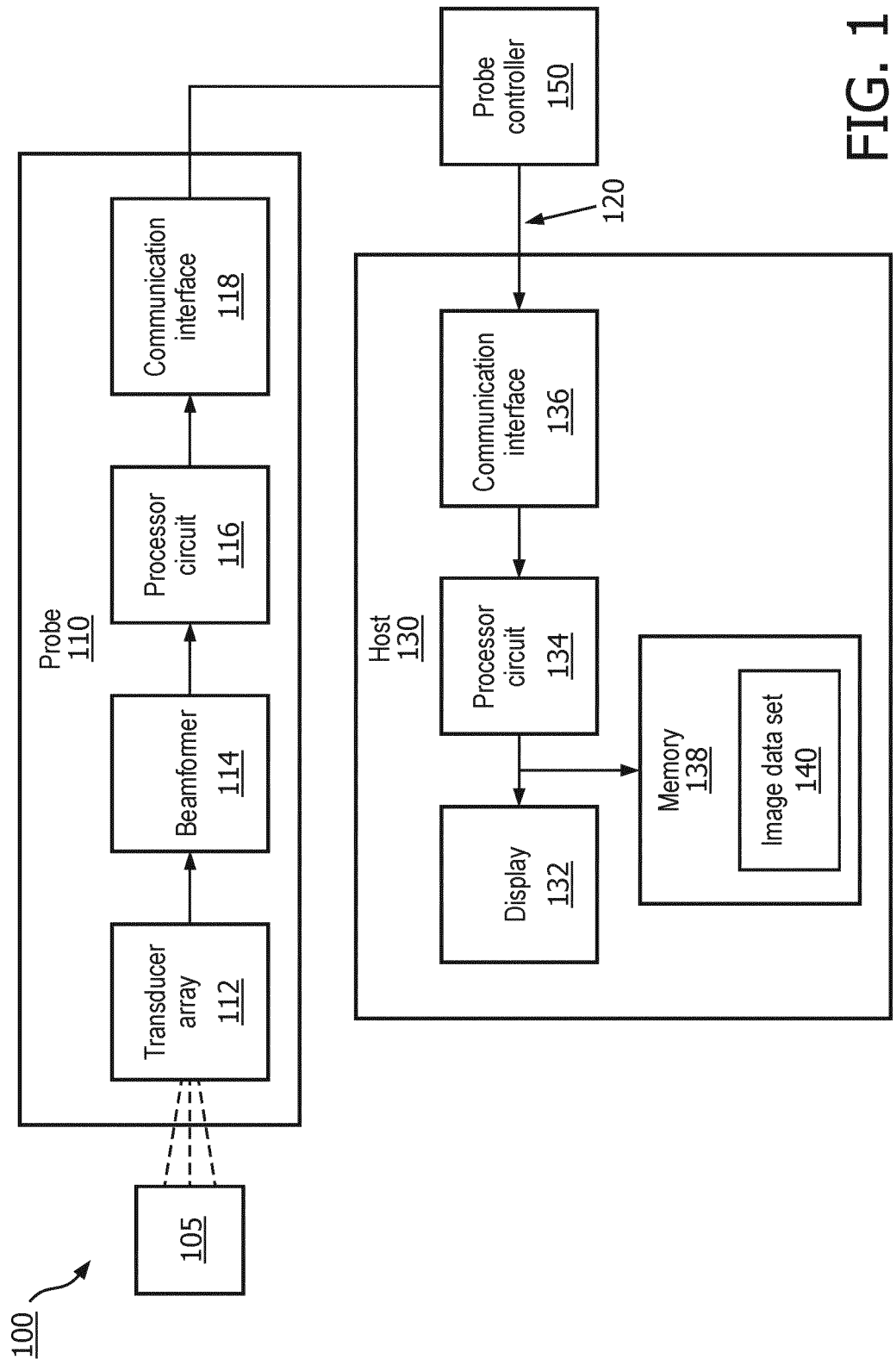
FIG. 1 is a schematic diagram of an ultrasound imaging system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a schematic diagram of an ultrasound imaging system 100, according to aspects of the present disclosure. The system 100 is used for scanning an area or volume of a patient's body. The system 100 includes an ultrasound imaging probe 110 in communication with a host 130 over a communication interface or link 120. The probe 110 includes a transducer array 112, a beamformer 114, a processor circuit 116, and a communication interface 118. The host 130 includes a display 132, a processor circuit 134, and a communication interface 136.

In an exemplary embodiment, the probe 110 is an external ultrasound imaging device including a housing configured for handheld operation by a user. The transducer array 112 can be configured to obtain ultrasound data while the user grasps the housing of the probe 110 such that the transducer array 112 is positioned adjacent to and/or in contact with a patient's skin. The probe 110 is configured to obtain ultrasound data of anatomy within the patient's body while the probe 110 is positioned outside of the patient's body. In some embodiment, the probe 110 can be an external ultrasound probe suitable for abdominal examination, for example, for diagnosing appendicitis or intussusception.

The transducer array 112 emits ultrasound signals towards an anatomical object 105 of a patient and receives echo signals reflected from the object 105 back to the transducer array 112. The ultrasound transducer array 112 can include any suitable number of acoustic elements, including one or more acoustic elements and/or plurality of acoustic elements. In some instances, the transducer array 112 includes a single acoustic element. In some instances, the transducer array 112 may include an array of acoustic elements with any number of acoustic elements in any suitable configuration. For example, the transducer array 112 can include between 1 acoustic element and 10000 acoustic elements, including values such as 2 acoustic elements, 4 acoustic elements, 36 acoustic elements, 64 acoustic elements, 128 acoustic elements, 500 acoustic elements, 812 acoustic elements, 1000 acoustic elements, 3000 acoustic elements, 8000 acoustic elements, and/or other values both larger and smaller. In some instances, the transducer array 112 may include an array of acoustic elements with any number of acoustic elements in any suitable configuration, such as a linear array, a planar array, a curved array, a curvilinear array, a circumferential array, an annular array, a phased array, a matrix array, a one-dimensional (1D) array, a 1.x dimensional array (e.g., a 1.5D array), or a two-dimensional (2D) array. The array of acoustic elements (e.g., one or more rows, one or more columns, and/or one or more orientations) that can be uniformly or independently controlled and activated. The transducer array 112 can be configured to obtain one-dimensional, two-dimensional, and/or three-dimensional images of patient anatomy. In some embodiments, the transducer array 112 may include a piezoelectric micromachined ultrasound transducer (PMUT), capacitive micromachined ultrasonic transducer (CMUT), single crystal, lead zirconate titanate (PZT), PZT composite, other suitable transducer types, and/or combinations thereof.

The object 105 may include any anatomy, such as blood vessels, nerve fibers, airways, mitral leaflets, cardiac structure, abdominal tissue structure, appendix, large intestine (or colon), small intestine, kidney, and/or liver of a patient that is suitable for ultrasound imaging examination. In some aspects, the object 105 may include at least a portion of a patient's large intestine, small intestine, cecum pouch, appendix, terminal ileum, liver, epigastrium, and/or psoas muscle. The present disclosure can be implemented in the context of any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood vessels, blood, chambers or other parts of the heart, abdominal organs, and/or other systems of the body. In some embodiments, the object 105 may include malignancies such as tumors, cysts, lesions, hemorrhages, or blood pools within any part of human anatomy. The anatomy may be a blood vessel, as an artery or a vein of a patient's vascular system, including cardiac vasculature, peripheral vasculature, neural vasculature, renal vasculature, and/or any other suitable lumen inside the body. In addition to natural structures, the present disclosure can be implemented in the context of man-made structures such as, but without limitation, heart valves, stents, shunts, filters, implants and other devices.

The beamformer 114 is coupled to the transducer array 112. The beamformer 114 controls the transducer array 112, for example, for transmission of the ultrasound signals and reception of the ultrasound echo signals. The beamformer 114 provides image signals to the processor circuit 116 based on the response of the received ultrasound echo signals. The beamformer 114 may include multiple stages of beamforming. The beamforming can reduce the number of signal lines for coupling to the processor circuit 116. In some embodiments, the transducer array 112 in combination with the beamformer 114 may be referred to as an ultrasound imaging component.

The processor circuit 116 is coupled to the beamformer 114. The processor circuit 116 may include a central processing unit (CPU), a graphical processing unit (GPU), a digital signal processor (DSP), an application specific integrated circuit (ASIC), a controller, a field programmable gate array (FPGA) device, another hardware device, a firmware device, or any combination thereof configured to perform the operations described herein. The processor circuit 134 may also be implemented as a combination of computing devices, e.g., a combination of a DSP and a microprocessor, a plurality of microprocessors, one or more microprocessors in conjunction with a DSP core, or any other such configuration. The processor circuit 116 is configured to process the beamformed image signals. For example, the processor circuit 116 may perform filtering and/or quadrature demodulation to condition the image signals. The processor circuit 116 and/or 134 can be configured to control the array 112 to obtain ultrasound data associated with the object 105.

The communication interface 118 is coupled to the processor circuit 116. The communication interface 118 may include one or more transmitters, one or more receivers, one or more transceivers, and/or circuitry for transmitting and/or receiving communication signals. The communication interface 118 can include hardware components and/or software components implementing a particular communication protocol suitable for transporting signals over the communication link 120 to the host 130. The communication interface 118 can be referred to as a communication device or a communication interface module.

The communication link 120 may be any suitable communication link. For example, the communication link 120 may be a wired link, such as a universal serial bus (USB) link or an Ethernet link. Alternatively, the communication link 120 may be a wireless link, such as an ultra-wideband (UWB) link, an Institute of Electrical and Electronics Engineers (IEEE) 802.11 WiFi link, or a Bluetooth link.

At the host 130, the communication interface 136 may receive the image signals. The communication interface 136 may be substantially similar to the communication interface 118. The host 130 may be any suitable computing and display device, such as a workstation, a personal computer (PC), a laptop, a tablet, or a mobile phone.

The processor circuit 134 is coupled to the communication interface 136. The processor circuit 134 may be implemented as a combination of software components and hardware components. The processor circuit 134 may include a central processing unit (CPU), a graphics processing unit (GPU), a digital signal processor (DSP), an application-specific integrated circuit (ASIC), a controller, a FPGA device, another hardware device, a firmware device, or any combination thereof configured to perform the operations described herein. The processor circuit 134 may also be implemented as a combination of computing devices, e.g., a combination of a DSP and a microprocessor, a plurality of microprocessors, one or more microprocessors in conjunction with a DSP core, or any other such configuration. The processor circuit 134 can be configured to generate image data from the image signals received from the probe 110. The processor circuit 134 can apply advanced signal processing and/or image processing techniques to the image signals. In some embodiments, the processor circuit 134 can form three-dimensional (3D) volume image from the image data. In some embodiments, the processor circuit 134 can perform real-time processing on the image data to provide a streaming video of ultrasound images of the object 105.

The display 132 is coupled to the processor circuit 134. The display 132 may be a monitor or any suitable display. The display 132 is configured to display the ultrasound images, image videos, and/or any imaging information of the object 105.

The system 100 may be used to assist a sonographer in performing an ultrasound scan, for example, at a point-of-care setting. For instance, the host 130 may be a mobile device, such as a tablet or a mobile phone. In some aspects, the sonographer may place the probe 110 on a patient to begin an ultrasound scan for a certain clinical evaluation, for example, for appendicitis or intussusception. The sonographer may follow a certain scanning topography or scanning trajectory commonly used or recommended for the clinical evaluation. The scanning topography or scanning trajectory may include a series of anatomical landmarks that may be relevant to the evaluation or may lead to a target anatomical site for the evaluation.

According to embodiments of the present disclosure, the system 100 may acquire an ultrasound image of the patient's anatomy at the initial position of the probe 110, determine a location within the patient's anatomy with respect to the scanning trajectory based on the image and/or an anatomical objected detected from the image, and determine a steering configuration for steering the probe 110 towards a next landmark along the scanning trajectory based on the determined location and/or the detected anatomical object. The system 100 may display graphical or visual indicators on the display 132 based on the steering configuration to guide the sonographer in steering the probe 110 towards the next landmark. The sonographer may steer the probe 110 based on the graphical or visual indicators. The system 100 may provide automated systematic scan guidance to the sonographer in real-time by repeatedly acquiring ultrasound images and determining steering configurations for steering the probe 110 towards a landmark along the scanning trajectory as the sonographer moves the probe 110. Additionally, the system 100 can automatically determine adjustments for ultrasound signal settings, such as signal gain and/or an imaging depth of field, and/or beam steering based on the acquired images. For instance, the system 100 may include a probe controller 150 configured to receive instruction from the host 130 and configure the transducer array 112 at the probe 110. Further, the system 100 can automatically capture or save one or more of the acquired images in the system 100 (e.g., at the memory 138) that are representative of a normal clinical condition for the clinical evaluation or an abnormal condition for the clinical evaluation so that the sonographer may review the captured or saved images after the scan.

In some aspects, the processor circuit 134 may implement one or more deep learning-based prediction networks trained to perform classification and/or prediction based on input ultrasound images. The classification and/or prediction may include classifying or identifying anatomical landmarks along a scanning trajectory for a certain clinical evaluation, predicting a steering configuration (e.g., including rotations and/or translations) for steering the probe 110 along the scanning trajectory and/or towards a certain target anatomical site, predicting a beam steering angle for configuring the transducer array 112 to reach a certain anatomical landmark or target site, predicting the presence or absence of a certain clinical condition, and/or predicting a ultrasound signal setting based on the quality of the image. Mechanisms for providing systematic scan assistance are described in greater detail herein.

In some aspects, the system 100 can be used for collecting ultrasound images to form training data set for deep learning network training. For example, the host 130 may include a memory 138, which may be any suitable storage device, such as a cache memory (e.g., a cache memory of the processor circuit 134), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, solid state drives, other forms of volatile and nonvolatile memory, or a combination of different types of memory. The memory 138 can be configured to store an image data set 140 to train a deep learning network in providing automatic scan assistance, automatic image capture, automatic ultrasound signal setting adjustments, and/or automatic beam steering. Mechanisms for training the prediction or deep learning networks are described in greater detail herein.

In clinical practices, when a patient is sent to an emergency room with an abdominal pain, an emergency physician may perform an abdominal scan to determine the cause of the abdominal pain. Two common causes of abdominal pain are appendicitis and intussusception. Appendicitis is the inflammation of the appendix (shown in FIG. 2). Intussusception is a medical condition in which one segment of the intestine telescopes inside of another segment of intestine, causing an intestinal obstruction or blockage (shown in FIG. 3).

Figure 2:
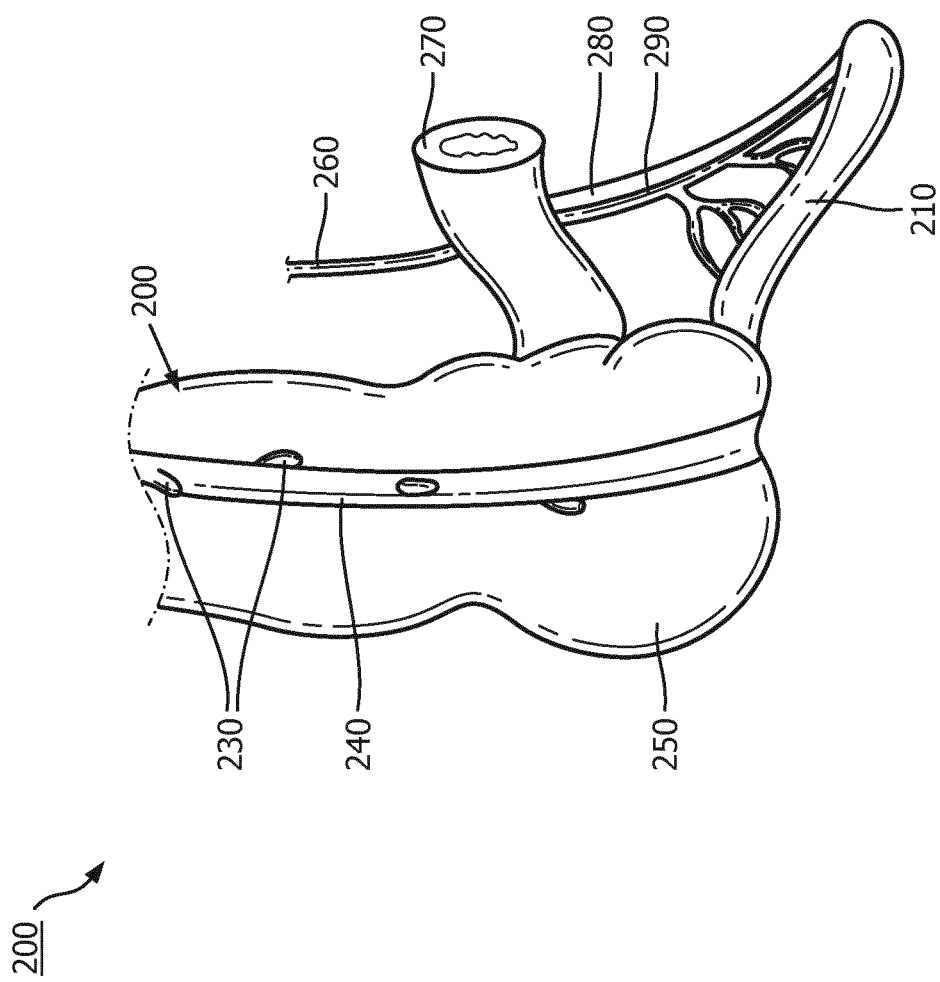
FIG. 2 is a schematic diagram of an appendix in an abdominal structure, according to aspects of the present disclosure.

FIG. 2 is a schematic diagram illustrating an appendix 210 in an abdominal structure 200, according to aspects of the present disclosure. The system 100 may be used to perform a scan around a patient's abdominal area (e.g., the abdominal structure 200) for evaluating an appendicitis condition. The appendix 210 is a closed tube of tissue attached to the large intestine 220 (also referred to as a colon) in the lower right abdomen. Inflammation occurs when the appendix 210 becomes infected or blocked. For instance, when the appendix 210 is inflamed, the appendix 210 may have a diameter larger than about 6 millimeters (mm). The sonographer may also use other characteristics to diagnose an appendicitis condition, for example, when the appendix 210 is fluid-filled. However, some of the structures surrounding or near the appendix 210, such as the appendix epiploicae 230, the *Taenia coli* 240, the cecum 250, the ileocolic artery 260, the ileum 270 (a final section of the small intestine), the mesoappendix 280, and/or the appendicular artery 290, can cause challenges in locating the appendix 210 during the scan.

Figure 3:
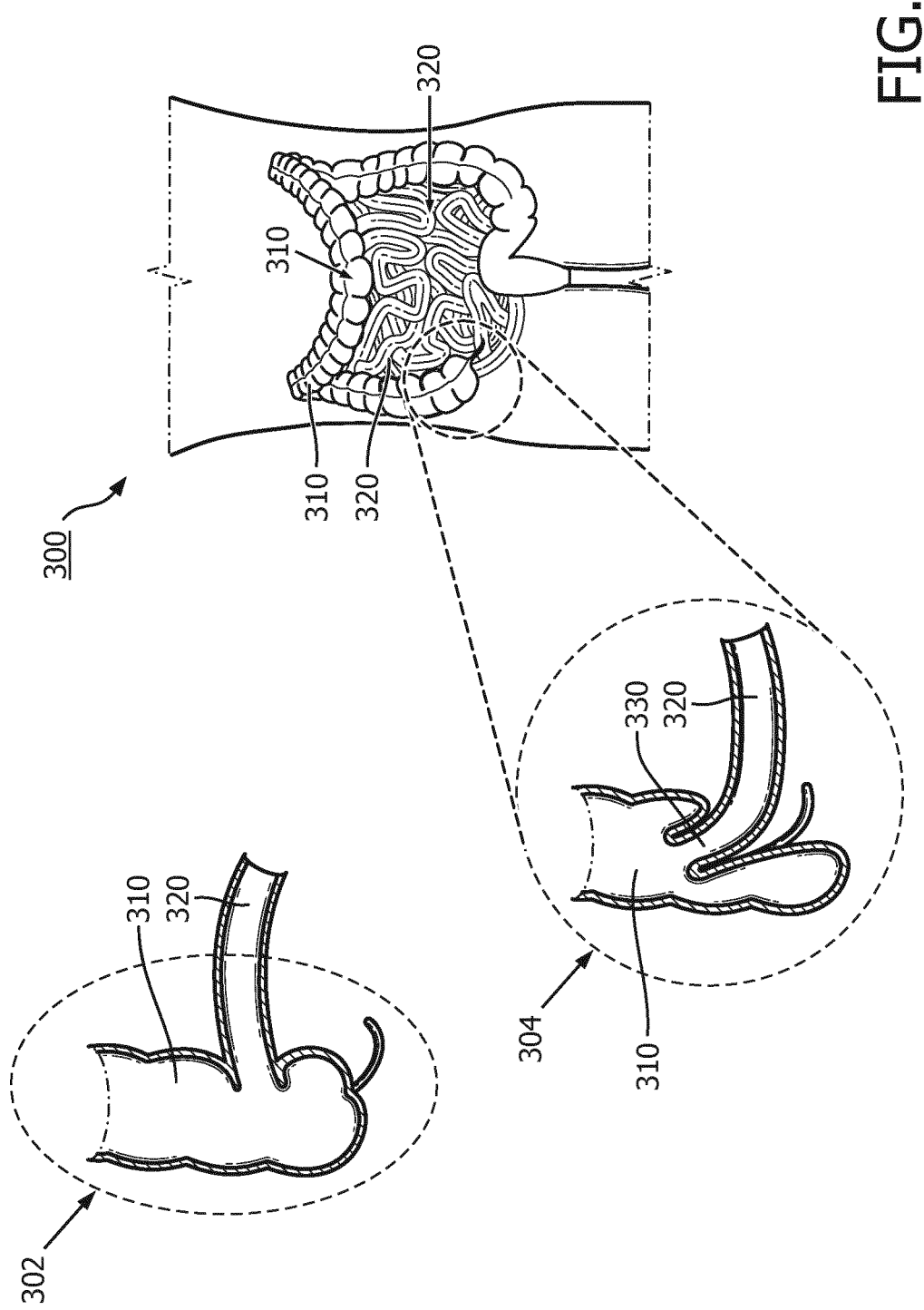
FIG. 3 is a schematic diagram illustrating an intussusception condition, according to aspects of the present disclosure.

FIG. 3 is a schematic diagram illustrating an intussusception condition 300, according to aspects of the present disclosure. The system 100 may be used to perform an abdominal scan for diagnosing the intussusception condition 300. Intussusception can occur anywhere in the gastrointestinal tract. One of the most common form of intussusception may be ileocolic intussusception, which occurs at the junction of the small and large intestines. FIG. 3 illustrates a portion of a patient's gastrointestinal tract including a large intestine 310 and a small intestine 320. A normal portion of the large intestine 310 is zoomed-in and shown as 302, where the small intestine 320 does not cause any obstruction or blockage to the large intestine 310. A portion of the large intestine 310 including an intussusception 330 is zoomed-in and shown as 304. At the site of the intussusception 330, a segment of the small intestine 320 folds into the large intestine 310, causing blockages.

For abdominal ultrasound scans, there are several abdominal topographies that physicians may use. One of the abdominal topographies that is preferred by many physicians is shown in FIG. 4A. FIG. 4A is a schematic diagram of an abdominal topography 400, according to aspects of the present disclosure. The system 100 can be used to perform a systematic abdominal scan according to the topography 400. As shown, the topography 400 divides a patient's abdominal area 402 by an axial line and a transverse line through the umbilicus into a right upper quadrant (RUQ) 410, a right lower quadrant (RLU) 420, a left upper quadrant (LUQ) 430, and a left lower quadrant (440). Scanning for appendicitis and intussusception requires systematic scanning and covering the topography 400 for clinical condition evaluation. However, an abdominal scan for diagnosing appendicitis may use a different trajectory over the topography 400 than an abdominal scan for diagnosing intussusception as shown and described below in FIG. 4B and FIG. 4C.

Figure 4B:
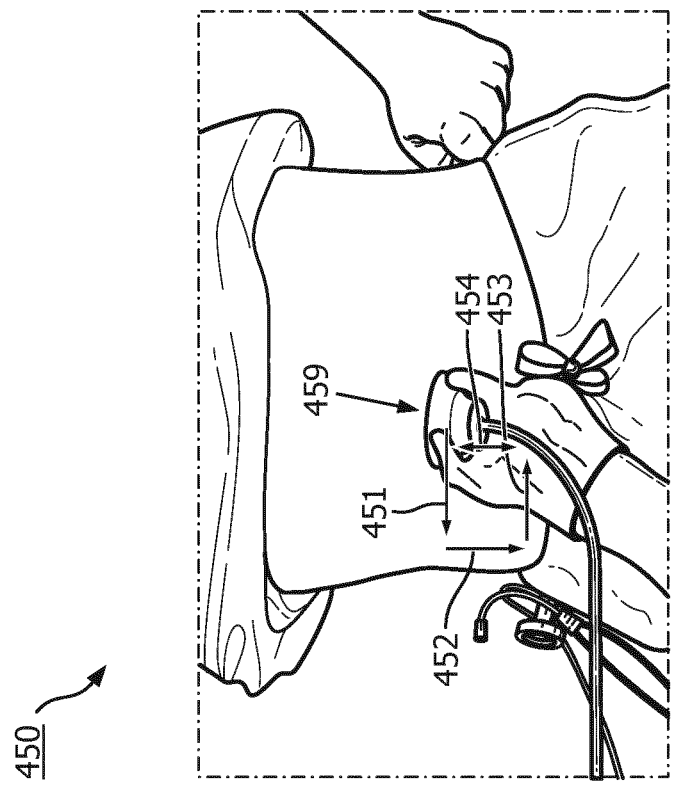
FIG. 4B is a schematic diagram illustrating a scanning trajectory for an appendicitis assessment, according to aspects of the present disclosure.
Figure 4A:
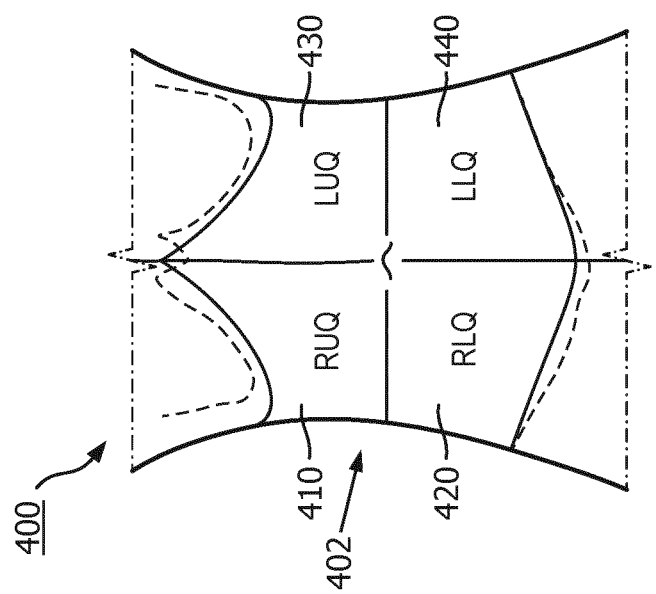
FIG. 4A is a schematic diagram of an abdominal topography, according to aspects of the present disclosure.

FIG. 4B is a schematic diagram illustrating a scanning trajectory 450 for an appendicitis assessment, according to aspects of the present disclosure. The system 100 may be used to perform an ultrasound scan according to the scanning trajectory 450. An appendicitis assessment may include a systematic scanning of the RLQ (e.g., the RLQ 420) of a patient. The scanning trajectory 450 covers the RLQ of the patient as shown by the arrows 451-454. For instance, a sonographer may place a probe 459 (e.g., the probe 110) transversely at an initial location in the RLQ near the umbilicus, sweep left as shown by the arrow 451, followed by sweeping down as shown by the arrow 452, sweeping right as shown by the arrow 453, and sweeping up and down as shown by the arrow 454 to locate the appendix (e.g., the appendix 210) for an appendicitis assessment.

FIG. 4C is a schematic diagram illustrating a scanning trajectory 460 for an intussusception assessment, according to aspects of the present disclosure. The system 100 may be used to perform an ultrasound scan according to the scanning trajectory 460. An intussusception assessment may include a systematic scanning of the entire abdominal topography (e.g., the topography 400), for example, in a lawn mow pattern. The scanning trajectory 460 are shown by the arrows 461-463. For instance, a sonographer may place a probe 469 (e.g., the probe 110) transversely at an initial location in the RLQ (e.g., the RLQ 420) of the patient, sweep up as shown by the arrow 461, followed by sweeping right as shown by the arrow 462 with the probe 459 placed longitudinally, and followed by sweeping down as shown by the arrow 463 with the probe 459 place transversely for an intussusception assessment.

While computerized tomography (CT) scan may be used for abdominal assessment, ultrasound is a preferred imaging modality due to the easy availability and lack of radiation. Additionally, the sensitivity and specificity of ultrasound is high, thus the use of ultrasound has become a common clinical practice for scanning for appendicitis or intussusception. Further, POCUS enables the ease of use and the availability of ultrasound at point-of-care settings.

However, for novice users, it is often challenging to perform serial, rapid, focused assessments in emergency settings. During ultrasound scanning of appendicitis or intussusception, an older child can point to the location of the pain but for younger patients, it requires systematic scanning. Though novice users can choose an initial location and try to follow a systematic approach, they may encounter several challenges while attempting to follow the ideal abdominal trajectory (e.g., the trajectories 450 and 460) to diagnose the condition. Some examples of challenges may include misidentification of the structure (e.g., misidentifying a terminal ileum or another component of the small bowel as the appendix), missed detection of the retrocecal (localized behind the cecum) appendicitis. The need to identify landmarks like ascending colon and/or wall of the colon and/or confirmation of sufficient scan coverage can also be challenging. Additionally, the identifying of features to support a certain diagnosis, for example, for appendicitis, such as measuring dilated appendix and determining whether the appendix has a diameter larger than 6 mm, searching for different clinical presentation of appendicolith (an appendicolith is composed of firm feces and some mineral deposits), identifying echogenic prominent peri-cecal fat, per-appendicular fluid collection, and/or searching for specific patterns (e.g., target like appearance appendix versus intussusception), can be time-consuming. Further, the use of ultrasound for diagnosis can be dependent on sonographer experiences.

Accordingly, the present disclosure provides techniques to automatically detect anatomical landmarks along a certain scanning trajectory or topography to provide systematic scan guidance to a sonographer. In some aspects, the present disclosure provides automatic probe steering guidance for scanning along a certain scanning trajectory relevant for a specific clinical examination, automatic capture of imaging frames that are representative of a normal clinical condition and/or an abnormal clinical condition to enable a quicker diagnosis, and/or automatic ultrasound signal setting adjustments for optimal imaging quality. In some aspects, the present disclosure may utilize a deep learning framework trained to provide automatic scanning guidance, auto-capture, and/or auto-signal-adjustments. Mechanisms for providing automatic scanning guidance, auto-capture, and/or auto-signal-adjustments are described in greater detail herein.

Figure 5:
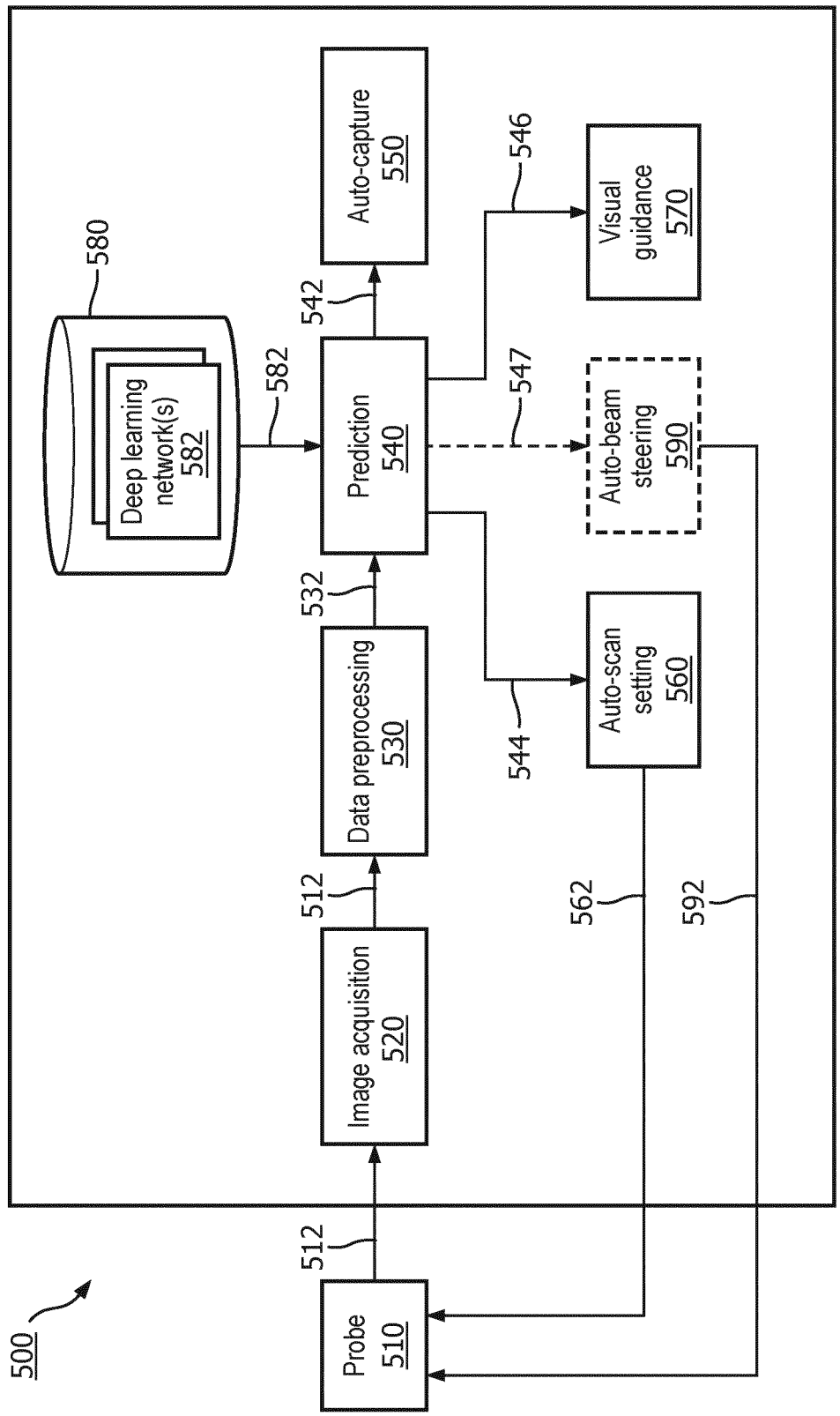
FIG. 5 is a schematic diagram of an automated ultrasound scanning assistance system, according to aspects of the present disclosure.

FIG. 5 is a schematic diagram of an automated ultrasound scanning assistance system 500, according to aspects of the present disclosure. The system 500 may correspond to the system 100, and may provide a detailed view of an implementation for providing ultrasound scanning assistance. At a high level, the system 500 automatically identifies anatomical landmarks from acquired images for a certain scanning trajectory (e.g., the trajectory 450 or 460) related to a clinical assessment, translate the identified information into user actions to provide a sonographer with systematic scan guidance. The system 500 can provide visual guidance to steer a probe (e.g., the probe 110) along the scanning trajectory and/or textual display of the automatically identified landmarks. Additionally, the system 500 automatically adjusts ultrasound signal gain settings (e.g., signal gain and/or signal depth) to provide an optimal imaging view. Further, the system 500 automatically captures and saves images frames that are relevant for a certain clinical assessment and tracks whether the scan includes a sufficient coverage for the clinical assessment.

The system 500 includes a probe 510, an image acquisition component 520, a data preprocessing component 530, a prediction component 540, a deep learning model repository 580, an auto-capture component 550, an auto-scan setting component 560, and a visual guidance component 570. The probe 510 may correspond to the probe 110 of FIG. 1 and may be capable of 2D imaging or 3D imaging. The visual guidance component 570 may correspond to the display 132 of FIG. 1. The image acquisition component 520, the data preprocessing component, 530, the prediction component 540, the auto-capture component 550, and/or the auto-scan setting component 560 may include hardware and/or software components. The image acquisition component 520 may include interfaces for receiving image frames from the probe 510. In some instances, the data preprocessing component, 530, the prediction component 540, the auto-capture component 550, and/or the auto-scan setting component 560 are implemented by the processor circuit 134. In some instances, the data preprocessing component, 530, the prediction component 540, the auto-capture component 550, and/or the auto-scan setting component 560 may be implemented by additional dedicated hardware configured for performing corresponding functions. The deep learning model repository 580 may include one or more trained deep learning networks 582 saved in a memory (e.g., the memory 138).

The probe 510 is configured to acquire ultrasound images 512. The images 512 are received by the image acquisition component 520. The images 512 may be brightness-mode (B-mode) images. The data preprocessing component 530 is configured to preprocess the imaging data 532 from the images 512 before passing the imaging data 532 to the prediction component 540. The preprocessing may include resizing the images 512, cropping a region of interest from the images 512, adjusting imaging gain, and/or any suitable image preprocessing.

The prediction component 540 receives the preprocessed imaging data 532. The imaging data 532 may be in the form of imaging frame. The prediction component 540 is configured to apply a trained deep learning network 582 stored in the deep learning model repository 580 to an input image 512. The deep learning network 582 performs the tasks of anatomical object classification and/or detection and probe steering prediction. In this regard, the deep learning network 582 may detect anatomical landmarks for a certain scanning trajectory and/or identifying a location of the probe 510 with respect to the scanning trajectory and/or landmarks from each acquired image 512. The deep learning network 582 may predict a steering configuration for steering the probe 510 to scan along the scanning trajectory based on the location of the probe 510 and/or the detected landmarks. The deep learning network 582 can be trained to identify landmarks for a certain scanning trajectory, for example, for an appendicitis evaluation or an intussusception evaluation, and infer a steering configuration based on identified landmarks. The detected landmarks served as the input to derive the steering actions. Some example anatomical landmarks along a scanning trajectory for appendicitis evaluation may include liver, ascending colon, cecum pouch, terminal ileum, appendix/appendicitis, and/or target signatures appendicitis. Some example anatomical landmarks along a scanning trajectory for intussusception evaluation may include psoas muscle, ascending colon, liver, gall bladder, epigastrium, descending colon, and target signatures of intussusception. The architecture of the deep learning network 582 is discussed in greater detail below in FIG. 6 and the training of the deep learning network is discussed in greater detail below in FIGS. 7 and 8. Scanning trajectories for appendicitis and intussusception are discussed in greater detail below in FIGS. 9 and 10.

The prediction component 540 outputs scan guidance information 546 predicted by the deep learning network 582 to the visual guidance component 570. The scan guidance information 546 may include the probe steering configuration and/or the identified landmarks. The steering configuration may include translations and/or rotations of the probe 510. The visual guidance component 570 is configured to translate the steering configuration into actions and display the actions as visual guidance to instruct the sonographer to steer the probe 510. The actions may include changing the probe 510 position, orientation, and/or direction. The visual guidance component 570 may also output the identified landmarks in textual form or display an acquired image 512 with the identified landmarks overlaid on top of the acquired image 512.

During a clinical examination, a sonographer may place the probe 510 on a patient at an initial location close to the scanning trajectory or somewhere along a starting position of the scanning trajectory. The probe 510 may acquire a first image 512 of the patient's anatomy. The deep learning network 582 may predict a steering configuration based on the first image 512 to steer the probe 510 towards a next landmark. The visual guidance component 570 may display steering instructions to guide the sonographer in steering the probe 510. The process of steering the probe 510, acquiring images, and predicting steering configurations based on the acquired images may continue until the scan covers the entire scanning trajectory. The clinical workflow and scan guidance are discussed in greater detail below in FIGS. 9 and 10.

In some aspects, the probe 510 may include a 2D transducer array capable of 3D imaging. The deep learning network 582 is trained to infer an ultrasound beam angle 547 from an input image 512 for steering ultrasound beams of the transducer array towards a target site (e.g., the appendix 210 or an intussusception 330) instead of instructing the sonographer to rotate the probe 510. The system 500 may include an electronic auto-beam steering component 590 configured to steer the ultrasound beams at the probe 510 based on the angle 547 predicted by the deep learning network 582. For instance, the electronic auto-beam steering component 590 can output a control signal 592 to adjust the beam angle at the probe 510.

Additionally, the deep learning network 582 is trained to determine whether an input image 512 has a good imaging quality or a bad imaging quality. In some instances, the prediction component 540 outputs indication 544 of the imaging quality. The indication 544 may indicate a good imaging quality or a bad imaging quality. The auto-scan setting component 560 receives the feedback (e.g., the indication 544) from the prediction component 540 and automatically determine an ultrasound signal setting adjustment for the probe 510. For instance, the adjustment may include a signal gain, for example, by controlling gain stages at the frontend of the probe 510. Additionally or alternatively, the adjustment may include an imaging depth of field adjustment, for example, by increasing or decreasing the ultrasound frequencies to decrease or increase the depth of view, respectively. The auto-scan setting component 560 outputs a control signal 562 to adjust the ultrasound signal setting at the probe 510 according to the indication 544. In some other instances, the deep learning network 582 is trained to infer an ultrasound signal setting (e.g., a signal gain or an imaging depth of field adjustment) based on the identified image quality and the prediction component 540 can instruct the auto-scan setting component 560 to adjust the ultrasound signal setting on the probe 510. While the auto-scan setting component 560 and the auto-beam steering component 590 are shown as separate components in FIG. 5, in some examples, the auto-scan setting component 560 and the auto-beam steering component 590 can be a single controller configured to control ultrasound signal setting and/or beam angle at the probe 510.

Further, the deep learning network 582 is trained to determine whether an input image 512 is relevant for a clinical diagnosis and output images 542 that are relevant for the diagnosis to the auto-capture component 550. The images 542 may include images with anatomical features representative of a normal condition and/or an abnormal condition for the clinical diagnosis. The auto-capture component 550 is configured to save the still image 542 to a memory (e.g., the memory 138) at the system 500. The sonographer may refer to the auto-captured or auto-saved image 542 to determine a clinical condition. Thus, the auto-captured or auto-saved image 542 can reduce time for the sonographer to search for relevant imaging frames for the clinical diagnosis.

In some aspects, the auto-capture component 550 may determine whether a sufficient coverage is achieved from the scan for the clinical assessment based on the acquired images 512. Alternatively, the deep learning network 582 is further trained to determine whether a sufficient coverage of the scanning trajectory had been scanned based on the captured images 512. If the scan does not include a sufficient coverage of the scanning trajectory for the clinical assessment, the prediction component 540 can continue to apply the deep learning network 582 to provide scanning guidance to the sonographer until the scan covers a sufficient coverage of the scanning trajectory.

In some aspects, the prediction component 540 may apply different trained deep learning networks from the deep learning model repository 580 for different types of predictions (e.g., classification, object detection, image quality prediction, auto-signal setting prediction, abnormal clinical condition/normal clinical condition prediction). In some aspects, the prediction component 540 may apply a single deep learning network for the predictions discussed above. In some aspects, the prediction component 540 may apply different deep learning networks for different types of predictions. For instance, the deep learning model repository 580 may include one deep learning network trained for probe steering motion prediction and another deep learning network trained for image quality or signal setting prediction. In some aspects, the prediction component 540 may apply different deep learning networks for different types of assessments. For instance, the deep learning model repository 580 may include one deep learning network trained to assist scanning for appendicitis assessment and another deep learning network trained to assist scanning for intussusception.

Figure 6:
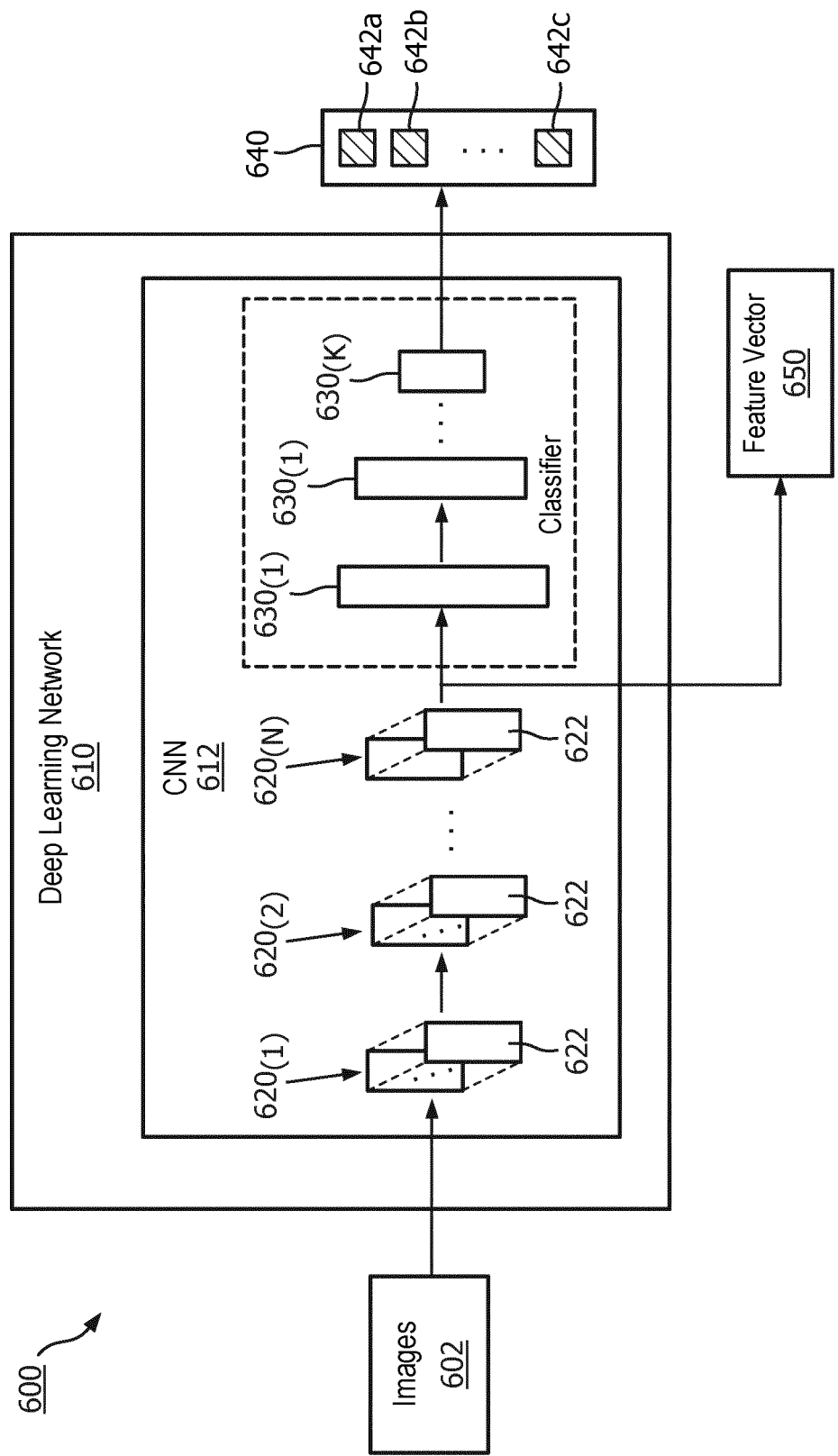
FIG. 6 is a schematic diagram of a deep learning network configuration, according to aspects of the present disclosure.

FIG. 6 is a schematic diagram of a deep learning network configuration 600, according to aspects of the present disclosure. The configuration 600 can be implemented by a deep learning network such as the deep learning network 582. The configuration 600 includes a deep learning network 610 including one or more CNNs 612. For simplicity of illustration and discussion, FIG. 6 illustrates one CNN 612. However, the embodiments can be scaled to include any suitable number of CNNs 612 (e.g., about 2, 3 or more). The configuration 600 can be trained for automated anatomical landmark detection, inference of probe steering configuration, image quality detection, and/or clinical condition detection as described in greater detail below.

The CNN 612 may include a set of N convolutional layers 620 followed by a set of K fully connected layers 630, where N and K may be any positive integers. The convolutional layers 620 are shown as $620_{(1)}$ to $620_{(N)}$. The fully connected layers 630 are shown as $630_{(1)}$ to $630_{(K)}$. Each convolutional layer 620 may include a set of filters 622 configured to extract features from an input 602 (e.g., images 512). The values N and K and the size of the filters 622 may vary depending on the embodiments. In some instances, the convolutional layers $620_{(1)}$ to $620_{(N)}$ and the fully connected layers $630_{(1)}$ to $630_{(K-1)}$ may utilize a leaky rectified non-linear (ReLU) activation function and/or batch normalization. The fully connected layers 630 may be non-linear and may gradually shrink the high-dimensional output to a dimension of the prediction result (e.g., the classification output 640). Thus, the fully connected layers 630 may also be referred to as a classifier.

The classification output 640 may indicate a confidence score for each class 642 based on the input image 602. The class 642 are shown as 642a, 642b, 642c. When the CNN 612 is trained for abdominal assessment, the classes 642 may indicate a liver class, an ascending colon class, a descending colon class, an appendix class, a cecum pouch class, and/or a psoas muscle class corresponding to landmarks along a scanning trajectory for the abdominal assessment. A class 642 indicating a high confidence score indicates that the input image 602 is likely to include an anatomical object of the class 642. Conversely, a class 642 indicating a low confidence score indicates that the input image 602 is unlikely to include an anatomical object of the class 642.

The CNN 612 can also output a feature vector 650 at the output of the last convolutional layer $620_{(N)}$. The feature vector 650 may indicate objects detected from the input image 602. For example, the feature vector 650 may indicate a liver, a diaphragm, and/or a kidney identified from the image 602.

Figure 7:
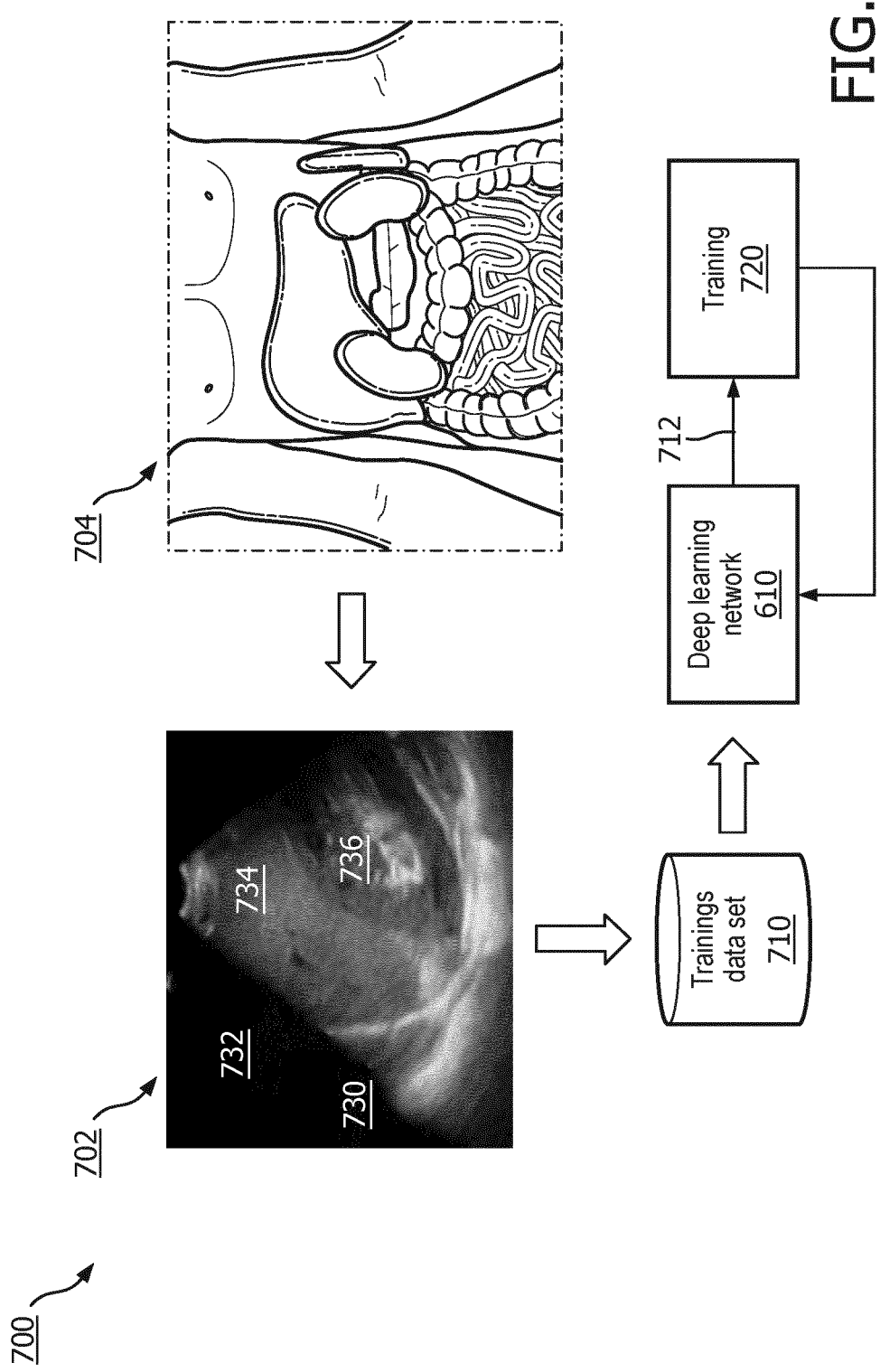
FIG. 7 is a schematic diagram of a deep learning network training scheme, according to aspects of the present disclosure.

FIG. 7 is a schematic diagram of a deep learning network training scheme 700 for providing scanning assistance in an appendicitis assessment, according to aspects of the present disclosure. The scheme 700 can be implemented by the systems 100 and 500. To train the deep learning network 610 to provide scanning assistance for an appendicitis assessment, a training data set 710 (e.g., the image data set 140) can be created. The training data set 710 may include annotated B-mode images. An expert may annotate the B-mode images with labels indicating anatomical objects and/or imaging artifacts. The B-mode images in the training data set 710 may include annotations for anatomical landmarks that are along a scanning trajectory (e.g., the trajectory 450) for appendicitis assessment. For instance, the B-mode images may include annotations for liver, ascending colon, cecum pouch, terminal ileum, appendix/appendicitis, and/or target signatures indicative of appendicitis.

In the illustrated example of FIG. 7, a B-mode image 702 is captured from a patient 704 and the image 702 is annotated by an expert with an annotation 730 for a mirror artifact, an annotation 732 for a diaphragm, an annotation 734 for a liver, and an annotation 736 for a kidney. The annotated image 702 is input to the deep learning network 610 for training. In some instances, the annotations may include bounding boxes in the area where the corresponding anatomical objects reside. The annotations 730, 732, 734, and 736 serve as the ground truths for training the deep learning network 610.

The deep learning network 610 can be applied to each image 702 in the data set, for example, using forward propagation, to obtain an output 712 for the input image 702. The training component 720 adjusts the coefficients of the filters 622 in the convolutional layers 620 and weightings in the fully connected layers 630, for example, by using backward propagation to minimize a prediction error (e.g., a difference between the ground truth and the prediction result 712). The prediction result 712 may include anatomical objects identified from the input image 702. In some instances, the training component 720 adjusts the coefficients of the filters 622 in the convolutional layers 620 and weightings in the fully connected layers 630 per input image. In some other instances, the training component 720 applies a batch-training process to adjust the coefficients of the filters 622 in the convolutional layers 620 and weightings in the fully connected layers 630 based on a prediction error obtained from a set of input images.

In some aspects, instead of including bounding boxes and annotations in a training image, the training data set 710 may store image-class pairs. For instance, each training image may be associated with a specific class (e.g., a liver, an ascending colon, a normal clinical condition, an abnormal clinical condition, a good imaging quality, or a bad imaging quality). The deep learning network 610 may be fed with the image-class pairs from the training data set 710 and the training component 720 can apply similar mechanisms to adjust the weightings in the convolutional layers 620 and/or the fully-connected layers 630 to minimize the prediction error between the ground truth (e.g., the specific class in the image-class pair) and the prediction output 712.

Figure 8:
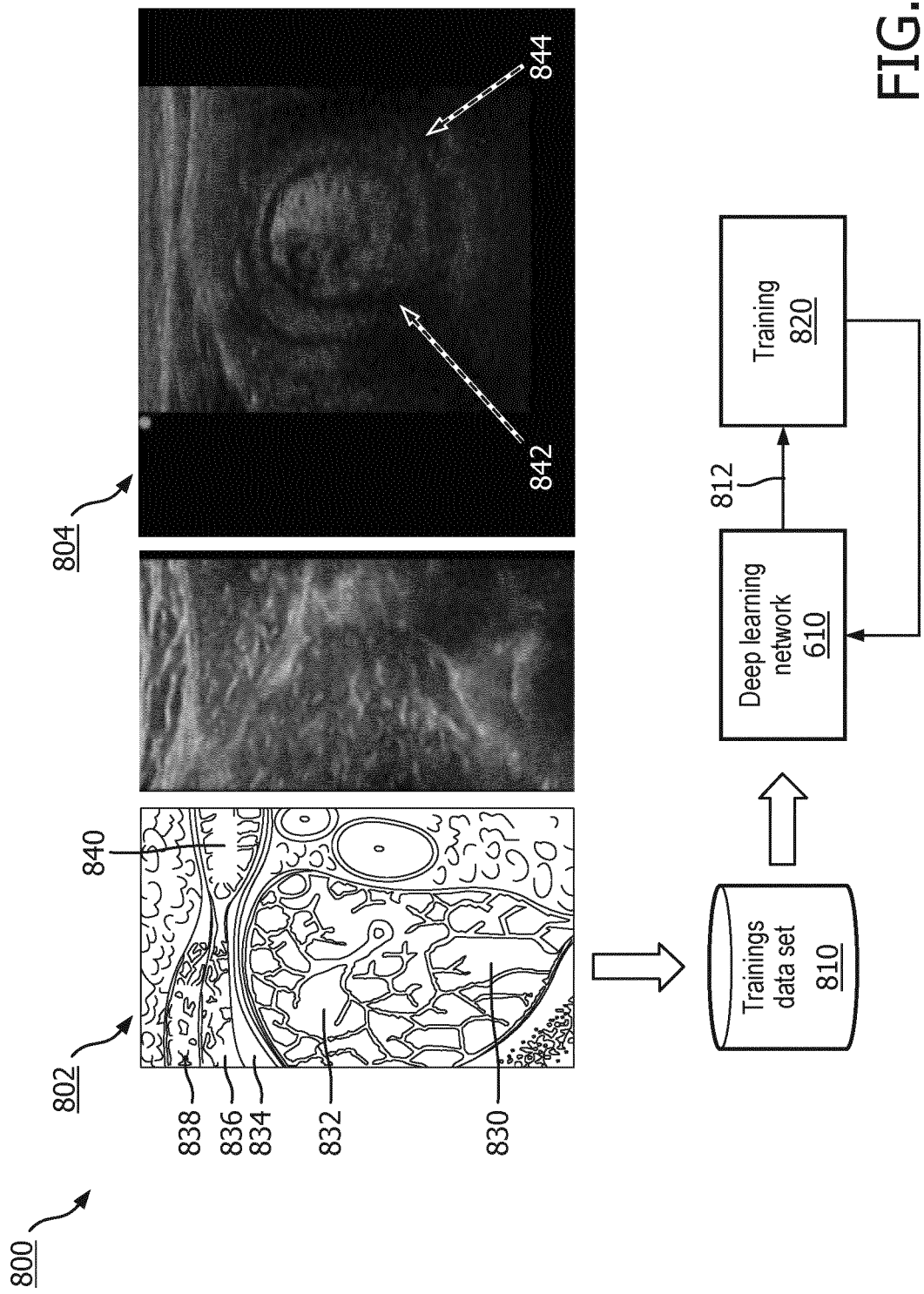
FIG. 8 is a schematic diagram of a deep learning network training scheme, according to aspects of the present disclosure.

FIG. 8 is a schematic diagram of a deep learning network training scheme 800 for providing scanning assistance in an intussusception assessment, according to aspects of the present disclosure. The scheme 800 can be implemented by the systems 100 and 500. The scheme 800 is substantially similar to the scheme 700, but may use a different training data set 810 including annotated images and/or image-class pairs specific to a scanning trajectory (e.g., the trajectory 460) for intussusception assessment. For instance, the B-mode images in the training data set 810 may include annotations or classes for psoas muscle, ascending colon, liver, gall bladder, epigastrium, descending colon, and target signatures of intussusception.

In the illustrated example of FIG. 8, the training data set 810 includes a B-mode image 802 is captured from a patient and the image 802 is annotated by an expert with an annotation 830 for an iliac crest, an annotation 832 for a psoas muscle, an annotation 834 for a transversus abdominal muscle, an annotation 836 for an internal oblique abdominal muscle, an annotation 838 for an external oblique abdominal muscle, and an annotation 840 for a rectus muscle. The training data set 810 may also include a B-mode image 804 including a target signature appearance of intussusception as shown by the labels 842 and 844.

The training component 820 can apply similar mechanisms as in the training component 720 to adjust the weightings in the convolutional layers 620 and/or the fully-connected layers 630 to minimize the prediction error between the ground truth and the prediction output 812 for each training image (e.g., the images 802 and 804). In some instances, the ground truth may correspond to the annotations of the anatomical objects and the prediction output 812 may include one or more anatomical objects (e.g., psoas muscle, rectus muscle, liver) identified from an input image. In some other instances, the ground truth may correspond to an image class and the prediction output 812 may include a predicted class (e.g., a psoas muscle class, a liver class, a normal clinical condition, an abnormal clinical condition, a good imaging quality, or a bad imaging quality).

Figure 9:
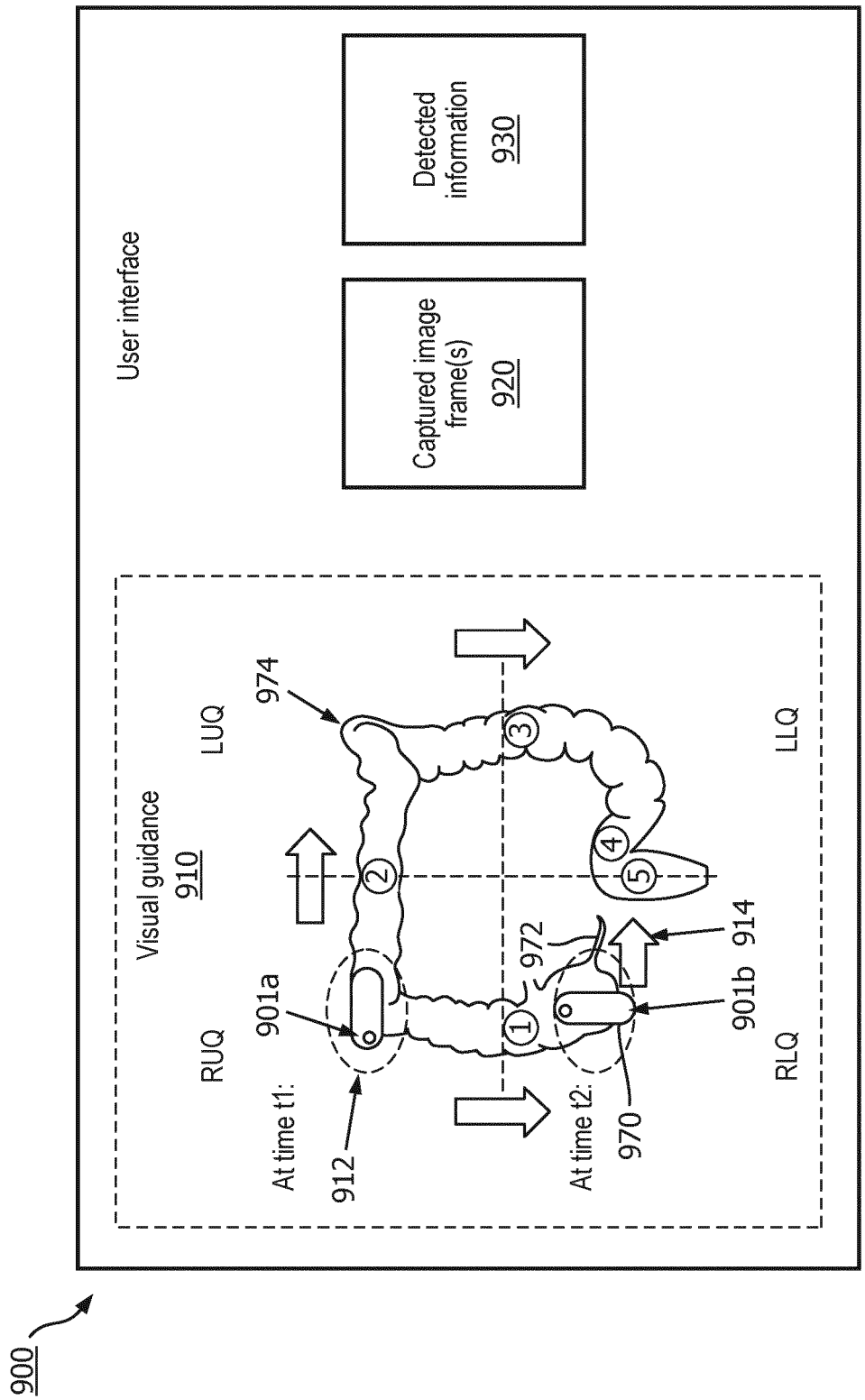
FIG. 9 is a schematic diagram of a user interface for an automated ultrasound scanning assistance system, according to aspects of the present disclosure.

FIG. 9 is a schematic diagram of a user interface 900 for an automated ultrasound scanning assistance system, according to aspects of the present disclosure. In particular, the user interface 900 can provide scanning assistance to a sonographer for an appendicitis assessment. The scanning may be along a scanning trajectory similar to the scanning trajectory 450 in an RLQ of a patient. The user interface 900 may be implemented by the system 500 and may be displayed on the visual guidance component 570 of FIG. 5. The user interface 900 is discussed in relation to FIG. 5 and may refer to the components shown in FIG. 5.

The user interface 900 incudes a visual guidance map 910. The visual guidance map 910 may illustrate an overall scan pattern (including a colon or large intestine 974 view of a patient under the scan) jointly with a depiction of the current transducer or probe position and orientation of the probe (shown by the transducer symbol 901). The probe position and/or orientation is inferred by the deep learning network 582 of FIG. 5. At time t1, a sonographer may place a probe 510 (shown by the transducer symbol 901) transversely at an initial location 912 on a patient's abdomen and capture a first image (e.g., the images 512). The deep learning network 582 may infer from the first input image, whether the first input image is located at a correct initial location or not. The deep learning network 582 may perform the inference based on one or more anatomical landmarks detected from the first input image. The anatomical landmarks may include to an ascending colon, a transvers colon, a descending colon, a sigmoid colon, and the rectum as shown by the circled numerals 1, 2, 3, 4, and 5, respectively. The one or more detected anatomical landmarks may serve as an input for determining whether the probe is at a correct location or not.

From the initial location 912, the deep learning network 582 infers a steering configuration (e.g., the steering configuration 546) to guide the sonographer in sweeping towards the RLQ (e.g., the RLQ 420), where landmarks such as a cecum pouch 970 (e.g., the cecum 250) is present. The cecum pouch 970 serves as a critical landmark to detect the close proximity of the appendix 972 (e.g., the appendix 210). The probe 510 may continue to capture images as the sonographer sweeps the probe 510.

While the sonographer sweeps the probe 510, the deep learning network 582 ensures the received input images include essential landmarks to infer the sweep operation is sufficiently correct. In this regard, the deep learning network 582 may search for landmarks of the ascending colon (circled numeral 1) from the captures images. If the deep learning network 582 determines that the landmarks of the ascending colon is not found in the captured images, the deep learning network 582 may infer a steering configuration for a corrected action and the visual guidance map 910 may show the action (e.g., in the form of arrows) to guide the user in correcting the position of the probe 510. For instance, if the deep learning network 582 detects that the ascending colon is drifting to the left in the image while the sonographer sweeps the probe 510 along the ascending colon (i.e., the probe 510 is drifting to the right of the ascending colon), then the deep learning network 582 may infer a steering configuration for moving the probe 510 to the left. The visual guidance map 910 may show a left arrow to suggest a course correction to the left in accordance with the steering configuration.

When the deep learning network 582 detected a next landmark (e.g., the cecum pouch 970) at time t2, the deep learning network 582 provides a different course of action. For instance, the deep learning network 582 may infer a probe steering configuration to physically rotate the probe 510 by about 90 degrees (as shown by the transducer symbol 901b) and move the probe 510 longitudinally (shown by 914). In some other instances, this operation can be achieved by automatic beam steering when the probe 510 is a 2D array matrix probe instead of having the sonographer to physically maneuver the probe 510. The 2D transducer array (e.g., the transducer array 112) at the probe 510 provides capability to select arbitrary imaging planes by appropriately phasing the transducer elements in the array. The 2D probe 510 can acquire images at various imaging planes and the images can be fed to the deep learning network 582 to infer a next imaging plane towards the target site where the appendix 972 is located.

During the longitudinal sweep 914, characteristics of the appendix 972 for appendicitis is inferred from the deep learning network 582. During this continuous sweep operation, the acquired images are fed into the auto-capture component 550 of FIG. 5 to conclude whether a sufficient scanning coverage is achieved or not. Alternatively, the deep learning network 582 can infer whether a sufficient scanning coverage is achieved based on the acquired images. Additionally, the acquired images are fed into the auto-scan setting component 560 of FIG. 5 to automatically adjust the ultrasound signal setting at the probe 510 to provide on optimal imaging quality for the assessment. Alternatively, the deep learning network 582 can infer an ultrasound signal setting for adjusting the ultrasound signal at the probe 510.

While FIG. 9 illustrates the guidance in the forms of arrows and orientation of the transducer suggesting a required action (e.g., translation and/or rotation) at the current position of the probe 510, the user interface 900 can provide the guidance in any suitable visual form and/or audio form (e.g., voice alerts). For instance, color-coded arrows may be used, where a red-colored arrow may indicate a deviation from the current scanning trajectory and a green arrow may indicate that the probe 510 is within the scanning trajectory. The deep learning network 582 may detect the deviation based on a certain landmark identified from an acquired image. The user interface 900 may further provide a voice alert indicating the deviation and a course correction.

The user interface 900 can further display one or more captured still image frames 920 that are indicative of a normal appendix or a suspected abnormal appendix (e.g., with inflammation or fluid-filled). The image frames 920 may correspond to the images 542. The user interface 900 can further display detected information 930, such as the anatomical objects and/or clinical condition identified from the captured images. The display can be in textual form or in the form of annotations overlaid on top of a captured image.

Figure 10:
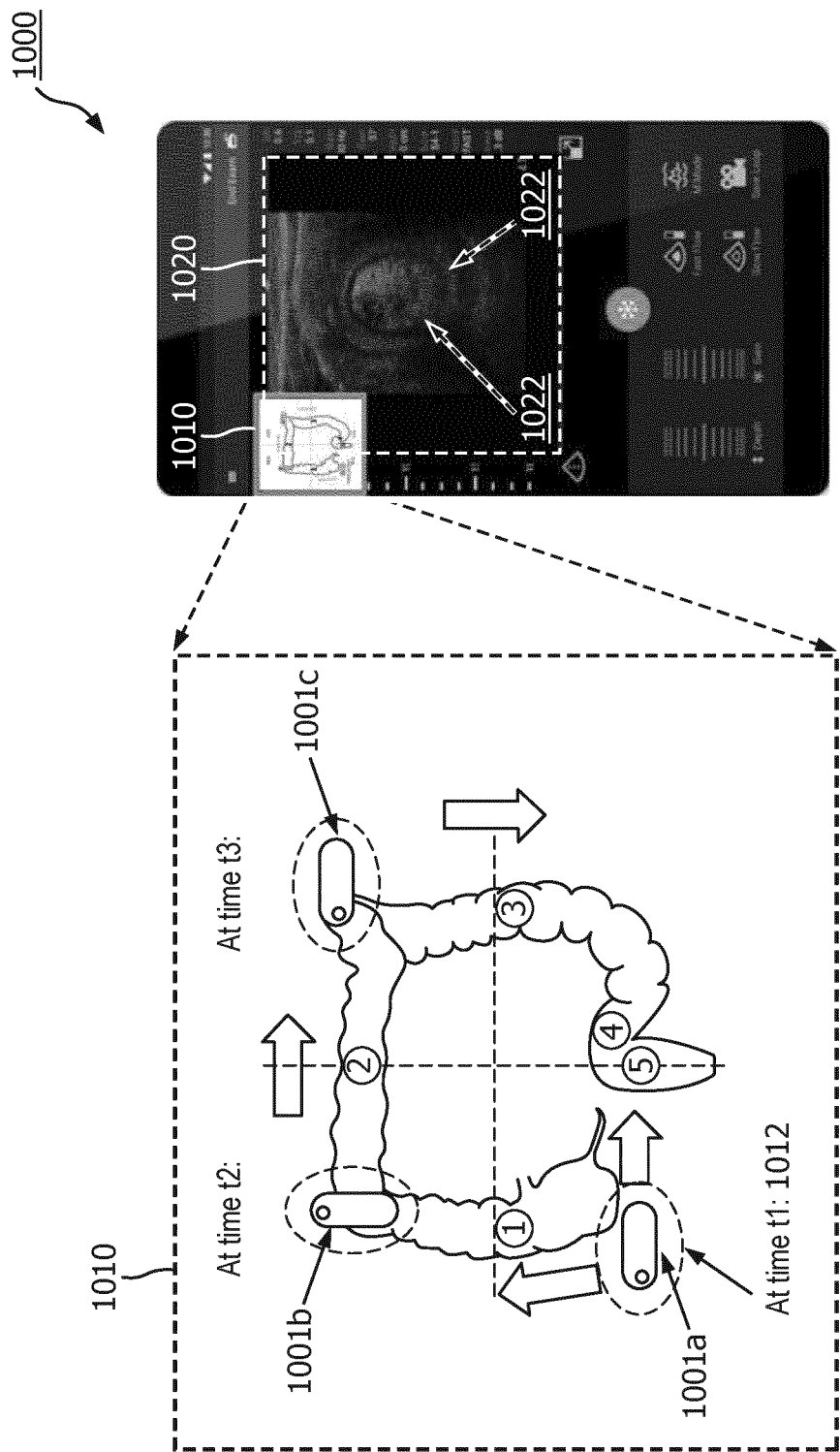
FIG. 10 is a schematic diagram of a user interface for an automated ultrasound scanning assistance system, according to aspects of the present disclosure.

FIG. 10 is a schematic diagram of a user interface 1000 for an automated ultrasound scanning assistance system, according to aspects of the present disclosure. In particular, the user interface 1000 can provide scanning assistance to a sonographer for an intussusception assessment. The user interface 1000 may be implemented by the system 500 and may be displayed on the visual guidance component 570 of FIG. 5. In the illustrated example of FIG. 10, the user interface 1000 is on the display of a mobile phone. In some other examples, the user interface 1000 can be displayed on any point-of-care devices. The user interface 1000 is discussed in relation to the FIG. 5 and may refer to components shown in FIG. 5. The user interface 1000 is substantially similar to the user interface 900. For instance, the user interface 1000 includes a visual guidance map 1010 similar to the visual guidance map 910 with similar landmarks shown by circled numerals 1-5. However, the visual guidance map 1010 may provide guidance for a different scanning trajectory specific for an intussusception assessment.

For instance, at time t1, the sonographer may place the probe 510 transversely at an initial location 1012 in an RLQ of a patient's abdomen (depicted as a transducer symbol 1001*a* on the map 1010) and capture a first input image. The deep learning network 582 of FIG. 5 may infer a steering configuration from the first input image to steer the probe towards the RUQ along the ascending colon (circled numeral 1). While the sonographer sweeps the probe 510, the probe 510 continues to acquire images and the images are fed to the deep learning network 582.

When the deep learning network 582 detected a next landmark such as a liver from an acquired image at time t2, the deep learning network 582 may infer a steering configuration to rotate the probe 510 by about 90 degrees to a longitudinal direction as shown by the transducer symbol 1001*b*. Alternatively, when the probe 510 is a 2D probe, this operation can be achieved via beam steering instead of a physical rotation of the probe 510 as described above with respect to FIG. 9. Subsequently, the deep learning network 582 may infer steering configurations to guide the sonographer to trace the probe 510 longitudinally till a next landmark (e.g., a spleen and/or a right kidney) is detected.

When the deep learning network 582 detected the next landmark at time t3, the deep learning network 582 may infer a steering configuration to rotate the probe 510 by about 90 degrees as shown by the transducer symbol 1001*c*. The deep learning network 582 may continue to infer steering configurations based on acquired images to guide the sonographer to trace till the LLQ of the patient covering the entire abdominal topography (from the RLQ to the RUQ to the LLQ).

Similar to the user interface 900, the user interface 1000 can further display one or more captured still image frames that are indicative of a normal clinical condition or the presence of a intussusception. In the illustrated example of FIG. 10, the user interface 1000 shows an image 1020 with markings 1022 at locations with suspected intussusception.

Figure 11:
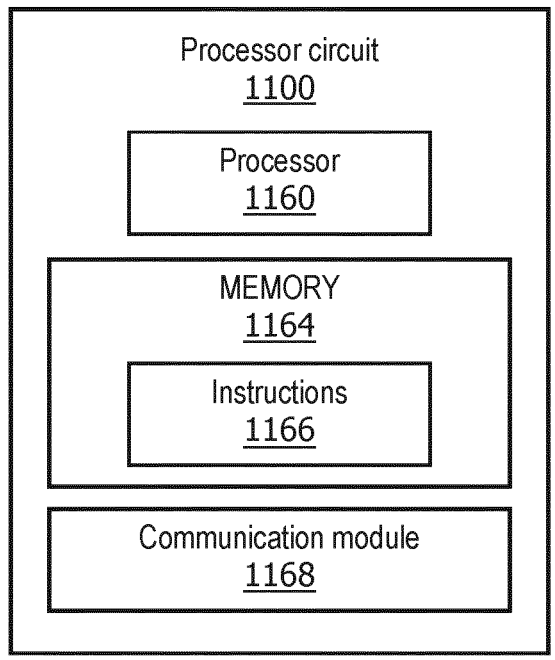
FIG. 11 is a schematic diagram of a processor circuit, according to embodiments of the present disclosure.

FIG. 11 is a schematic diagram of a processor circuit 1100, according to embodiments of the present disclosure. The processor circuit 1100 may be implemented in the probe 110 and/or the host 130 of FIG. 1. In an example, the processor circuit 1100 may be in communication with the transducer array 112 in the probe 110. As shown, the processor circuit 1100 may include a processor 1160, a memory 1164, and a communication module 1168. These elements may be in direct or indirect communication with each other, for example via one or more buses.

The processor 1160 may include a CPU, a GPU, a DSP, an application-specific integrated circuit (ASIC), a controller, an FPGA, another hardware device, a firmware device, or any combination thereof configured to perform the operations described herein, for example, aspects of FIGS. 5-10, and 12. The processor 1160 may also be implemented as a combination of computing devices, e.g., a combination of a DSP and a microprocessor, a plurality of microprocessors, one or more microprocessors in conjunction with a DSP core, or any other such configuration.

The memory 1164 may include a cache memory (e.g., a cache memory of the processor 1160), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, other forms of volatile and non-volatile memory, or a combination of different types of memory. In an embodiment, the memory 1164 includes a non-transitory computer-readable medium. The memory 1164 may store instructions 1166. The instructions 1166 may include instructions that, when executed by the processor 1160, cause the processor 1160 to perform the operations described herein, for example, aspects of FIGS. 5-10 and 12 and with reference to the probe 110 and/or the host 130 (FIG. 1). Instructions 1166 may also be referred to as code. The terms "instructions" and "code" should be interpreted broadly to include any type of computer-readable statement (s). For example, the terms "instructions" and "code" may refer to one or more programs, routines, sub-routines, functions, procedures, etc. "Instructions" and "code" may include a single computer-readable statement or many computer-readable statements.

The communication module 1168 can include any electronic circuitry and/or logic circuitry to facilitate direct or indirect communication of data between the processor circuit 1100, the probe 110, and/or the display 132. In that regard, the communication module 1168 can be an input/output (I/O) device. In some instances, the communication module 1168 facilitates direct or indirect communication between various elements of the processor circuit 1100 and/or the probe 110 (FIG. 1), the probe 510 (FIG. 5) and/or the host 130 (FIG. 1)

Figure 12:
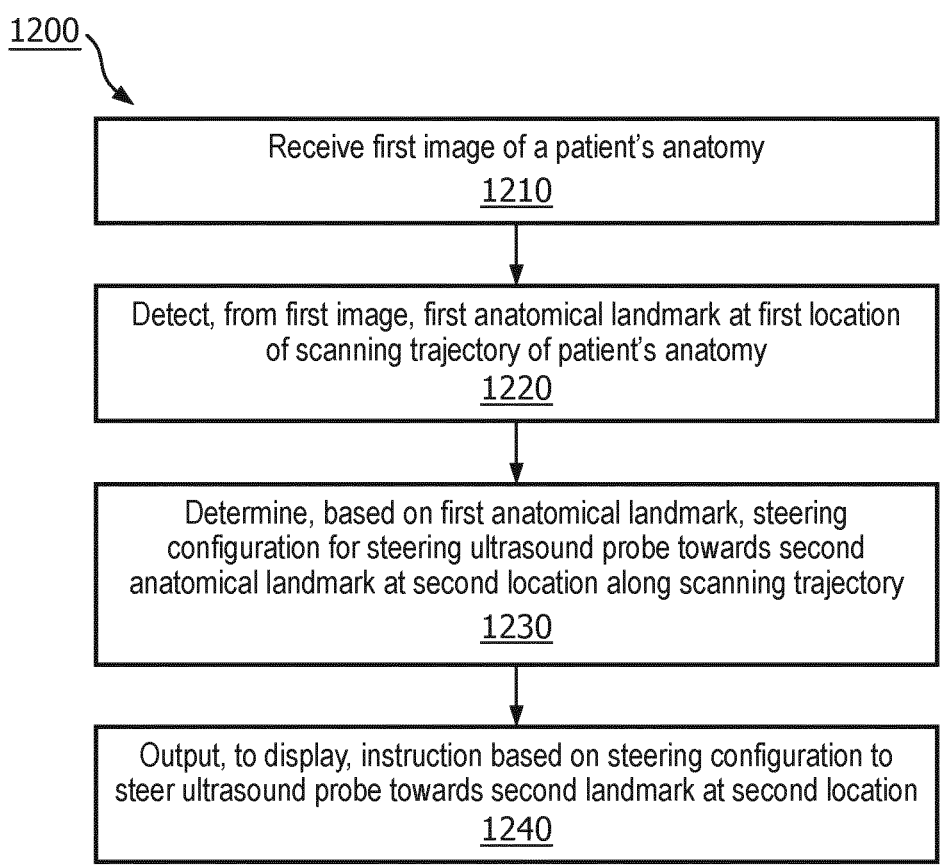
FIG. 12 is a flow diagram of an ultrasound imaging method, according to aspects of the present disclosure.

FIG. 12 is a flow diagram of an ultrasound imaging method 1200 with automatic assistance, according to aspects of the present disclosure. The method 1200 is implemented by the system 100, for example, by a processor circuit such as the processor circuit 1100, and/or other suitable component such as the probe 110 or 510, the processor circuit 116, the host 130, and/or the processor circuit 134. In some examples, the system 100 can include computer-readable medium having program code recorded thereon, the program code comprising code for causing the system 100 to execute the steps of the method 1200. The method 1200 may employ similar mechanisms as in the systems 100 and 500 described with respect to FIGS. 1 and 5, respectively, the configuration 600 described with respect to FIG. 6, the schemes 700 and 800 described with respect to FIGS. 7 and 8, respectively, and the user interfaces 900 and 1000 described with respect to FIGS. 9 and 10, respectively. As illustrated, the method 1200 includes a number of enumerated steps, but embodiments of the method 1200 may include additional steps before, after, and in between the enumerated steps. In some embodiments, one or more of the enumerated steps may be omitted or performed in a different order.

At step 1210, the method 1200 includes receiving, at a processor circuit (e.g., the processor circuits 134 and 1100) in communication with an ultrasound probe (e.g., the probes 110 and 510) including a transducer array (e.g., the transducer array 112), a first image (e.g., the images 512) of a patient's anatomy.

At step 1220, the method 1200 includes detecting, at the processor circuit from the first image, a first anatomical landmark at a first location along a scanning trajectory (e.g., the scanning trajectories 450 and 460) of the patient's anatomy.

At step 1230, the method 1200 includes determining, at the processor circuit based on the first anatomical landmark, a steering configuration (e.g., the steering configuration 546) for steering the ultrasound probe towards a second anatomical landmark at a second location along the scanning trajectory.

At step 1240, the method 1200 includes outputting, to a display in communication with the processor circuit, an instruction based on the steering configuration to steer the ultrasound probe towards the second anatomical landmark at the second location.

In some instances, the steering configuration includes at least one of a rotation or a translation.

In some instances, the method 1200 further includes receiving, at the processor circuit from the ultrasound probe, a second image of the patient's anatomy at the second location, the second image including the second anatomical landmark. The method 1200 further includes determining, at the processor circuit based on the second image, a beam steering angle to steer ultrasound beams of the transducer array towards a third anatomical landmark at a third location along the scanning trajectory. The method 1200 further includes outputting, to a controller in communication with the processor circuit and the ultrasound probe, an instruction to configure the transducer array based on the beam steering angle. The controller may be similar to the probe controller 150 and/or the auto-beam steering component 590.

In some instances, the method 1200 further includes determining, at the processor circuit, an ultrasound signal adjustment for the transducer array based on the first image. The method 1200 further includes outputting, to a controller in communication with the processor circuit and the transducer probe, an instruction to configure the transducer array based on the ultrasound signal adjustment. In some instances, the ultrasound signal adjustment is associated with at least one of a signal gain or an imaging depth of field. The controller may be similar to the probe controller 150 and/or the auto-scan setting component 560.

In some instances, the method 1200 further includes receiving, at the processor circuit from the transducer array, a second image of the patient's anatomy at the second location along the scanning trajectory. The method 1200 further includes determining, at the processor circuit, that the second image includes an anatomical feature representative of a clinical condition. The method 1200 further includes storing, at a memory (e.g., the memory 138) in communication with the processor circuit, the second image based on determining that the second image includes the anatomical feature representative of the clinical condition.

In some instances, the step 1240 includes outputting, to the display, a map of the scanning trajectory and at least one of a visual motion indicator with respect to the scanning trajectory based on the instruction, a location of the transducer array with respect to the scanning trajectory, or an orientation of the transducer array with respect to the scanning trajectory, for example, as shown in the visual guidance maps 910 or 1010.

In some instances, the patient's anatomy includes an abdominal region of the patient, and wherein the scanning trajectory traverses at least one of a RUQ (e.g., the RUQ 410), a RLQ (e.g., the RLQ 420), a LUQ (e.g., the LUQ 430), or a LLQ (e.g., the LLQ 440) of the patient's abdominal region.

In some instances, the scanning trajectory is associated with an appendicitis examination, and wherein the first anatomical landmark includes at least one of a liver, an ascending colon, a cecum pouch, a terminal ileum, an appendix, or an anatomical characteristic of an appendicitis.

In some instances, the scanning trajectory is associated with an intussusception examination, and wherein the first anatomical landmark includes at least one of a psoas muscle, an ascending colon, a liver, a gallbladder, an epigastrium, a descending colon, an anatomical characteristic of an intussusception.

Aspects of the present disclosure can provide several benefits. For example, the use of a deep learning-based framework for automated anatomical landmark detection and probe steering motion prediction can provide a clinician with systematic scanning guidance, reducing ultrasound examination time and/or user-dependency. Thus, the disclosed embodiments may increase the accuracy of clinical assessments (e.g., appendicitis and intussusception assessments) and improve work flow efficiency.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An ultrasound imaging system comprising:
a processor circuit configured for communication with an ultrasound probe comprising a transducer array,
wherein the processor circuit is configured to control the ultrasound probe to perform ultrasound imaging along a scanning trajectory of a patient's anatomy,
wherein the scanning trajectory comprises a starting position, a first anatomical landmark, and a second anatomical landmark,
wherein the first anatomical landmark and the second anatomical landmark are distinct from the starting position,
wherein the first anatomical landmark and the second anatomical landmark are indicative of a clinical condition such that the scanning trajectory is pre-determined based on an assessment for the clinical condition,
wherein, to control the ultrasound probe to perform the ultrasound imaging along the scanning trajectory, the processor circuit is configured to:
receive, from the ultrasound probe, a first image of a patient's anatomy;
detect, from the first image, the first anatomical landmark;
determine, based on the first anatomical landmark, a steering configuration for steering the ultrasound probe towards the second anatomical landmark; and output, to a display in communication with the processor circuit, an instruction based on the steering configuration to steer the ultrasound probe towards the second anatomical landmark.

2. The system of claim 1, wherein the steering configuration includes at least one of a rotation or a translation.

3. The system of claim 1, further comprising:
a probe controller in communication with the ultrasound probe and the processor circuit,
wherein the transducer array is a two-dimensional (2D) transducer array, and
wherein the processor circuit is configured to:
receive, from the ultrasound probe, a second image of the patient's anatomy, the second image including the second anatomical landmark;
determine, based on the second image, a beam steering angle to steer ultrasound beams of the transducer array towards a third anatomical landmark; and
output, to the probe controller, an instruction to configure the transducer array based on the beam steering angle.

4. The system of claim 1, wherein the processor circuit configured to detect the first anatomical landmark and determine the steering configuration is configured to:
apply a predictive network to the first image, the predictive network trained for at least one of an anatomical landmark detection or a steering configuration prediction associated with the scanning trajectory.

5. The system of claim 1, further comprising:
a probe controller in communication with the ultrasound probe and the processor circuit,
wherein the processor circuit is configured to:
receive, from the ultrasound probe, a second image of the patient's anatomy, the second image including the second anatomical landmark;
apply a predictive network to the second image, the predictive network trained for beam steering prediction; and
output, to the probe controller, an instruction to configure the transducer array based on an output of the predictive network.

6. The system of claim 1, further comprising:
a probe controller in communication with the ultrasound probe and the processor circuit,
wherein the processor circuit is configured to:
receive, from the ultrasound probe, a second image of the patient's anatomy based on the steering configuration;
apply a predictive network to the second image, the predictive network trained for at least one of an ultrasound signal gain adjustment or an imaging depth of field adjustment; and
output, to the probe controller, an instruction to configure the transducer array based on an output of the predictive network.

7. The system of claim 1, further comprising:
a memory in communication with the processor circuit,
wherein the processor circuit is configured to:
receive, from the ultrasound probe, a second image of the patient's anatomy based on the steering configuration;
apply a predictive network to the second image, the predictive network trained to identify a clinical condition; and
store, at the memory, the second image based on an output of the predictive network.

8. The system of claim 1, wherein the processor circuit configured to output the instruction is configured to:
output, to the display, a map of the scanning trajectory and at least one of a visual motion indicator with respect to the scanning trajectory based on the instruction, a location of the transducer array with respect to the scanning trajectory, or an orientation of the transducer array with respect to the scanning trajectory.

9. The system of claim 1, wherein the patient's anatomy includes an abdominal region of the patient, and wherein the scanning trajectory traverses at least one of a right upper quadrant (RUQ), a right lower quadrant (RLQ), a left upper quadrant (LUQ), or a left lower quadrant (LLQ) of the patient's abdominal region.

10. The system of claim 1, wherein the scanning trajectory is associated with an appendicitis examination, and wherein the first anatomical landmark includes at least one of:
a liver;
an ascending colon;
a cecum pouch;
a terminal ileum;
an appendix; or
an anatomical characteristic of an appendicitis.

11. The system of claim 1, wherein the scanning trajectory is associated with an intussusception examination, and wherein the first anatomical landmark includes at least one of:
a psoas muscle;
an ascending colon;
a liver;
a gallbladder;
an epigastrium;
a descending colon; or
an anatomical characteristic of an intussusception.

12. The system of claim 1, further comprising:
a probe controller in communication with the ultrasound probe and the processor circuit,
wherein the processor circuit is configured to:
determine an ultrasound signal adjustment for the transducer array based on the first image; and
output, to the probe controller, an instruction to configure the transducer array based on the ultrasound signal adjustment.

13. The system of claim 12, wherein the ultrasound signal adjustment is associated with at least one of a signal gain or an imaging depth of field.

14. The system of claim 1, further comprising:
a memory in communication with the processor circuit,
wherein the processor circuit is configured to:
receive, from the ultrasound probe, a second image of the patient's anatomy based on the steering configuration;
determine that the second image includes an anatomical feature representative of a clinical condition; and
store, at the memory, the second image based on determining that the second image includes the anatomical feature representative of the clinical condition.

15. The system of claim 14, wherein the processor circuit is configured to:
output, to the display, the second image based on determining that the second image includes the anatomical feature representative of the clinical condition.

16. A method of ultrasound imaging, comprising:
controlling, by a processor circuit, an ultrasound probe to perform ultrasound imaging along a scanning trajectory of a patient's anatomy, wherein the ultrasound probe comprises a transducer array, wherein the scanning trajectory comprises a starting position, a first anatomical landmark, and a second anatomical landmark, wherein the first anatomical landmark and the second anatomical landmark are distinct from the starting position, wherein the first anatomical landmark and the second anatomical landmark are indicative of a clinical condition such that the scanning trajectory is pre-determined based on an assessment for the clinical condition, wherein controlling the ultrasound probe to perform ultrasound imaging comprises:
receiving a first image of a patient's anatomy;
detecting, from the first image, the first anatomical landmark;
determining, based on the first anatomical landmark, a steering configuration for steering the ultrasound probe towards the second anatomical landmark; and
outputting, to a display in communication with the processor circuit, an instruction based on the steering configuration to steer the ultrasound probe towards the second anatomical landmark.

17. The method of claim 16, wherein the steering configuration includes at least one of a rotation or a translation.

18. The method of claim 16, further comprising:
receiving, at the processor circuit from the ultrasound probe, a second image of the patient's anatomy, the second image including the second anatomical landmark;

determining, at the processor circuit based on the second image, a beam steering angle to steer ultrasound beams of the transducer array towards a third anatomical landmark; and
outputting, to a probe controller in communication with the processor circuit and the ultrasound probe, an instruction to configure the transducer array based on the beam steering angle.

19. The method of claim 16, further comprising:
determining, at the processor circuit, an ultrasound signal adjustment for the transducer array based on the first image, the ultrasound signal adjustment associated with at least one a signal gain or an imaging depth of field; and
outputting, to a probe controller in communication with the processor circuit and the ultrasound probe, an instruction to configure the transducer array based on the ultrasound signal adjustment.

20. The method of claim 16, further comprising:
receiving, at the processor circuit from the ultrasound probe, a second image of the patient's anatomy based on the steering configuration;
determining, at the processor circuit, that the second image includes an anatomical feature representative of a clinical condition; and
storing, at a memory in communication with the processor circuit, the second image based on determining that the second image includes the anatomical feature representative of the clinical condition.

* * * * *